(12) United States Patent
Snyder et al.

(10) Patent No.: US 8,388,654 B2
(45) Date of Patent: Mar. 5, 2013

(54) METHOD AND APPARATUS FOR ATTACHING SOFT TISSUE TO BONE

(75) Inventors: Nathan B. Snyder, Los Angeles, CA (US); George J. Rohlinger, Coeur d'Alene, ID (US)

(73) Assignee: Redyns Medical LLC, Los Angeles, CA (US)

( * ) Notice: Subject to any disclaimer, the term of this patent is extended or adjusted under 35 U.S.C. 154(b) by 926 days.

(21) Appl. No.: 12/239,585

(22) Filed: Sep. 26, 2008

(65) Prior Publication Data

US 2009/0088798 A1 Apr. 2, 2009

Related U.S. Application Data

(60) Provisional application No. 60/995,304, filed on Sep. 26, 2007, provisional application No. 61/083,244, filed on Jul. 24, 2008, provisional application No. 61/077,375, filed on Jul. 1, 2008, provisional application No. 61/048,587, filed on Apr. 29, 2008, provisional application No. 61/041,766, filed on Apr. 2, 2008, provisional application No. 61/011,402, filed on Jan. 17, 2008, provisional application No. 61/002,713, filed on Nov. 9, 2007.

(51) Int. Cl.
*A61B 17/04* (2006.01)
(52) U.S. Cl. ..................................................... 606/232
(58) Field of Classification Search .................. 606/232, 606/300, 301, 304; 411/21
See application file for complete search history.

(56) References Cited

U.S. PATENT DOCUMENTS

| | | | |
|---|---|---|---|
| 5,217,486 A * | 6/1993 | Rice et al. | 606/232 |
| 5,681,352 A | 10/1997 | Clancy, III et al. | |
| 5,906,624 A | 5/1999 | Wenstrom, Jr. | |
| 5,957,953 A * | 9/1999 | DiPoto et al. | 606/232 |
| 6,733,506 B1 | 5/2004 | McDevitt et al. | |
| 7,217,279 B2 | 5/2007 | Reese | |
| 7,322,978 B2 * | 1/2008 | West, Jr. | 606/60 |
| 7,585,311 B2 | 9/2009 | Green et al. | |
| 2002/0052629 A1 * | 5/2002 | Morgan et al. | 606/232 |
| 2003/0120309 A1 * | 6/2003 | Colleran et al. | 606/232 |
| 2004/0133239 A1 * | 7/2004 | Singhatat | 606/232 |
| 2005/0222618 A1 * | 10/2005 | Dreyfuss et al. | 606/232 |
| 2005/0283158 A1 * | 12/2005 | West, Jr. | 606/73 |
| 2006/0004364 A1 * | 1/2006 | Green et al. | 606/72 |
| 2006/0106423 A1 * | 5/2006 | Weisel et al. | 606/232 |
| 2006/0259076 A1 | 11/2006 | Burkhart et al. | |
| 2007/0005068 A1 | 1/2007 | Sklar | |
| 2007/0135843 A1 | 6/2007 | Burkhart | |
| 2009/0082807 A1 * | 3/2009 | Miller et al. | 606/232 |
| 2009/0118776 A1 * | 5/2009 | Kelsch et al. | 606/325 |

* cited by examiner

*Primary Examiner* — Melanie Tyson
*Assistant Examiner* — Son Dang
(74) *Attorney, Agent, or Firm* — Dunlap Codding, P.C.

(57) ABSTRACT

A soft tissue repair system comprising:
at least one anchor, the at least one anchor comprising a body, a bone-engaging element attached to the body for securing the body in bone, and a suture-attaching element attached to the body for attaching suture to the anchor, the suture-attaching element being configured so as to permit suture to be snared by the suture-attaching element after the anchor has been deployed in the bone.

11 Claims, 35 Drawing Sheets

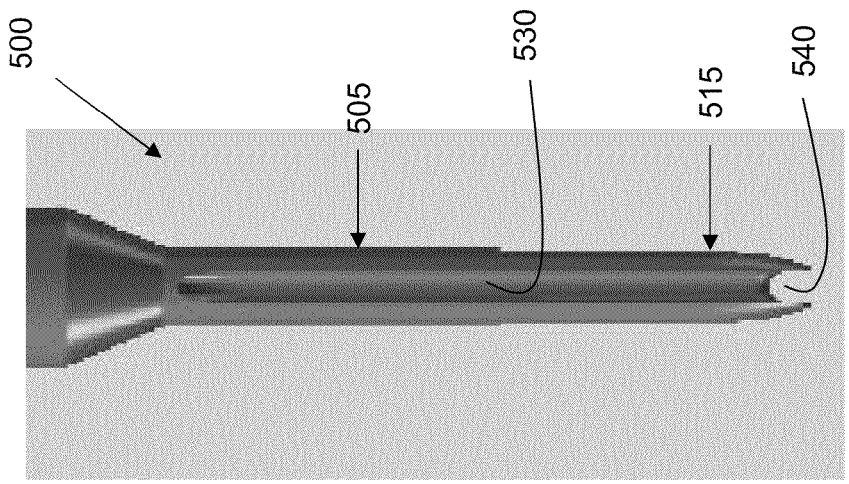
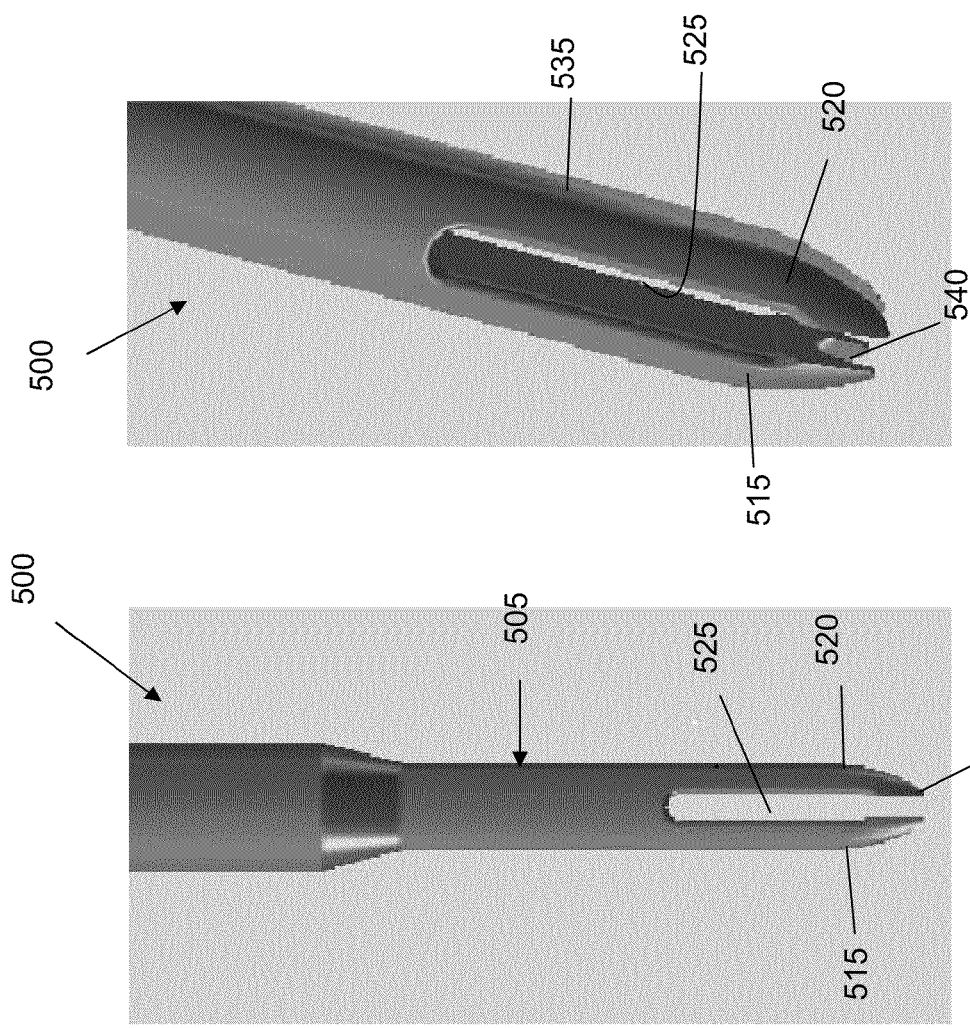
FIG. 36
FIG. 35
FIG. 34

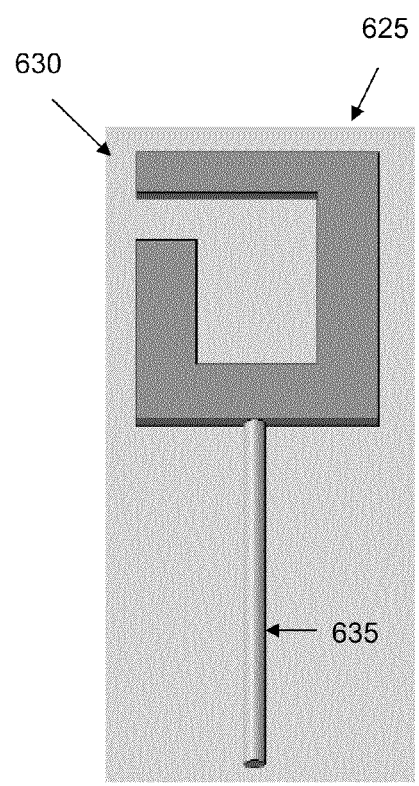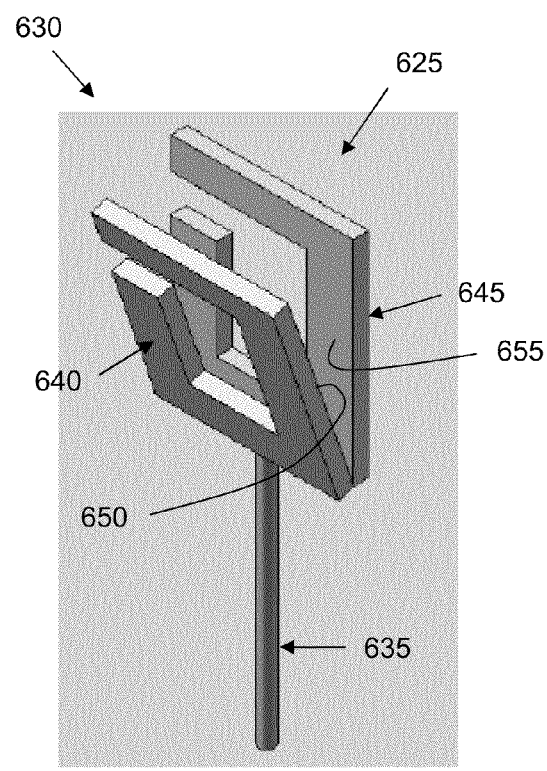
FIG. 47
FIG. 48

METHOD AND APPARATUS FOR ATTACHING SOFT TISSUE TO BONE

REFERENCE TO PENDING PRIOR PATENT APPLICATIONS

This patent application claims benefit of:

(i) pending prior U.S. Provisional Patent Application Ser. No. 60/995,304, filed Sep. 26, 2007 by George J. Rohlinger et al. for SURGICAL IMPLANT AND TECHNIQUE;

(ii) pending prior U.S. Provisional Patent Application Ser. No. 61/002,713, filed Nov. 9, 2007 by George J. Rohlinger et al. for SURGICAL IMPLANT AND TECHNIQUE;

(iii) pending prior U.S. Provisional Patent Application Ser. No. 61/011,402, filed Jan. 17, 2008 by George J. Rohlinger et al. for SURGICAL IMPLANT AND TECHNIQUE;

(iv) pending prior U.S. Provisional Patent Application Ser. No. 61/041,766, filed Apr. 2, 2008 by George J. Rohlinger et al. for SUTURE ANCHOR;

(v) pending prior U.S. Provisional Patent Application Ser. No. 61/048,587, filed Apr. 29, 2008 by George J. Rohlinger et al. SUTURE ANCHOR;

(vi) pending prior U.S. Provisional Patent Application Ser. No. 61/077,375, filed Jul. 1, 2008 by George J. Rohlinger et al. for SUTURE ANCHOR; and (vii) pending prior U.S. Provisional Patent Application Ser. No. 61/083,244, filed Jul. 24, 2008 by George J. Rohlinger et al. for SUTURE ANCHOR.

The seven (7) above-identified patent applications are hereby incorporated herein by reference.

FIELD OF THE INVENTION

This invention relates to surgical methods and apparatus in general, and more particularly to surgical methods and apparatus for attaching soft tissue to bone.

BACKGROUND OF THE INVENTION

In many situations soft tissue may need to be attached (or re-attached) to bone. By way of example but not limitation, a ligament or tendon may have been detached from bone as the result of injury and/or accident, and appropriate repair may require re-attaching the ligament or tendon to its host bone. By way of further example but not limitation, some surgical procedures may require the suspension of soft tissue from an adjacent bone, e.g., a so-called "bladder neck suspension" may involve suspending portions of the bladder and/or urethra from the pubic bone in order to address incontinence.

Currently, suture anchors are typically used to attach soft tissue to bone. Such suture anchors generally comprise a body and one or more sutures attached to the body. In use, the body of the suture anchor is deployed in bone so that the one or more sutures extend out of the bone. The one or more sutures may then be used to secure the soft tissue to the bone, e.g., by passing the one or more sutures through the soft tissue and then knotting the suture so as to hold the soft tissue in position relative to the bone.

Unfortunately, current suture anchors generally suffer from several disadvantages.

First, current suture anchors have their one or more sutures attached to the suture anchor either at the time of manufacture or in the operating room just prior to use. In either case, the one or more sutures are attached to the body of the suture anchor prior to deployment of the suture anchor in the body. As a result, during surgery, the surgeon is constrained by the configuration of the suture anchor once it has been deployed in the body. In other words, with current suture anchor constructions, the particular anchor body/suture configuration selected by the surgeon prior to deployment in the bone significantly constrains the choices available to the surgeon after the suture anchor has been deployed in the bone. This can be a significant limitation, since in many circumstances the surgeon may wish to adjust a procedure in response to tissue conditions which may only become apparent after the procedure has begun.

In addition to the foregoing, it can be difficult and/or inconvenient for the surgeon to knot the suture when physical access to the surgical site is limited, e.g., as in the case of an arthroscopic procedure.

As a result, one object of the present invention is to provide a new and improved suture anchor for attaching soft tissue to bone which permits the surgeon to attach one or more sutures to the body of the suture anchor after the body of the suture anchor has been deployed in bone, thereby allowing the surgeon to customize the manner in which the soft tissue is attached to the bone.

Another object of the present invention is to provide a surgeon with the ability to modify a soft tissue repair construct, in part or in whole, without removing any previously-deployed anchors forming part of the repair construct.

And another object of the present invention is to provide a new and improved suture anchor for attaching soft tissue to bone which permits the soft tissue to be attached to the bone without tying a knot in the suture.

SUMMARY OF THE INVENTION

The present invention comprises the provision and use of a new suture anchor system for attaching soft tissue to bone which permits the surgeon to attach one or more sutures to the body of the suture anchor after the body of the suture anchor has been deployed in bone, thereby allowing the surgeon to customize the manner in which the soft tissue is attached to the bone. Significantly, the present invention provides a surgeon with the ability to modify a soft tissue repair construct, in part or in whole, without removing any previously-deployed anchors forming part of the repair construct. Furthermore, the present invention permits the soft tissue to be attached to the bone without tying a knot in the suture.

In one preferred form of the present invention, there is provided a soft tissue repair system comprising:

at least one anchor, the at least one anchor comprising a body, a bone-engaging element attached to the body for securing the body in bone, and a suture-attaching element attached to the body for attaching suture to the anchor, the suture-attaching element being configured so as to permit suture to be snared by the suture-attaching element after the anchor has been deployed in the bone.

In another preferred form of the present invention, there is provided a method for attaching soft tissue to bone, the method comprising:

providing a soft tissue repair system, the soft tissue repair system comprising:

at least one anchor, the at least one anchor comprising a body, a bone-engaging element attached to the body for securing the body in bone, and a suture-attaching element attached to the body for attaching suture to the anchor, the suture-attaching element being configured so as to permit suture to be snared by the suture-attaching element after the anchor has been deployed in the bone;

deploying the at least one anchor in the bone; and presenting at least one suture to the at least one anchor so that the at least one suture is snared by the suture-attaching element, whereby to attach the at least one suture to the at least one anchor.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein:

FIGS. 34-36 are schematic views of another suture threader which may be used in accordance with the present invention;

FIGS. 45-48 are schematic views illustrating a soft tissue grasping mechanism.

DETAILED DESCRIPTION OF THE INVENTION

Figure 1:
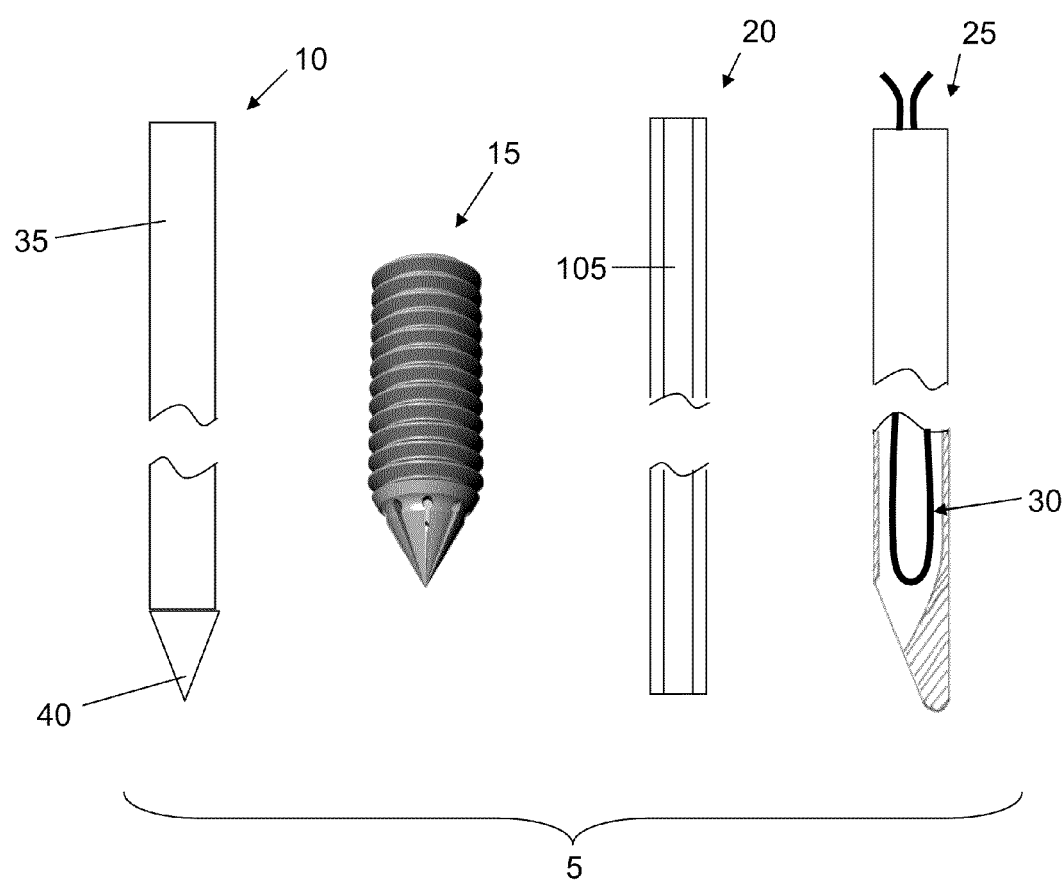
FIG. 1 is a schematic view showing a suture anchor system comprising a pilot drill, an anchor, a driver and a suture threader.

Looking first at FIG. 1, there is shown a suture anchor system 5 formed in accordance with the present invention. Suture anchor system 5 generally comprises a pilot drill 10, an anchor 15, a driver 20 and a suture threader 25 carrying a suture 30 therein.

Still looking now at FIG. 1, pilot drill 10 is a conventional pilot drill of the sort used to form a pilot hole in bone. Pilot drill 10 generally comprises a shaft 35 terminating in a distal point 40.

Figures 2, 3:
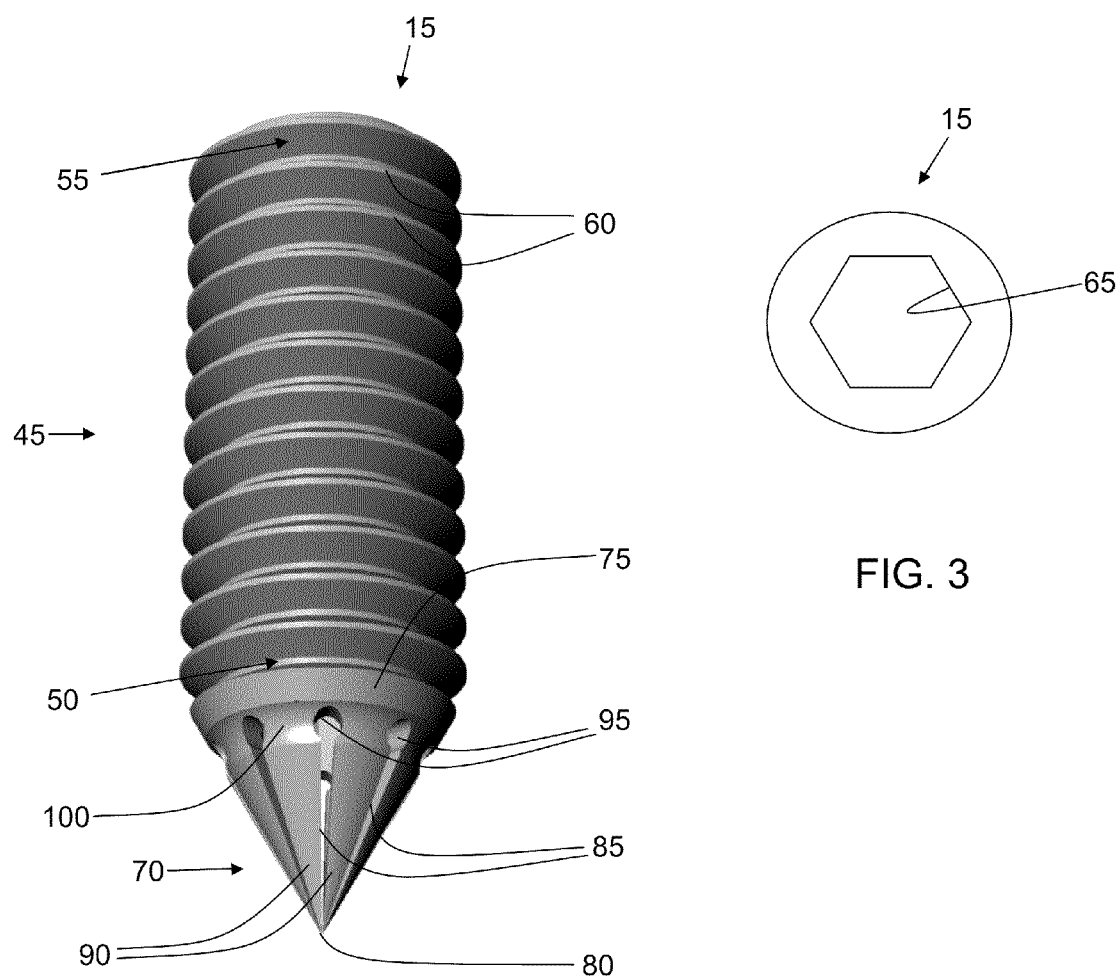
FIGS. 2 and 3 are schematic views showing the anchor of the system of FIG. 1.

Looking next at FIGS. 1-3, anchor 15 generally comprises a cylindrical body 45 having a distal end 50 and a proximal end 55. Screw threads 60 extend from distal end 50 to proximal end 55. A non-circular (e.g., hexagonal) bore 65 extends from distal end 50 to proximal end 55. Cylindrical body 45 is substantially rigid.

Figure 9:
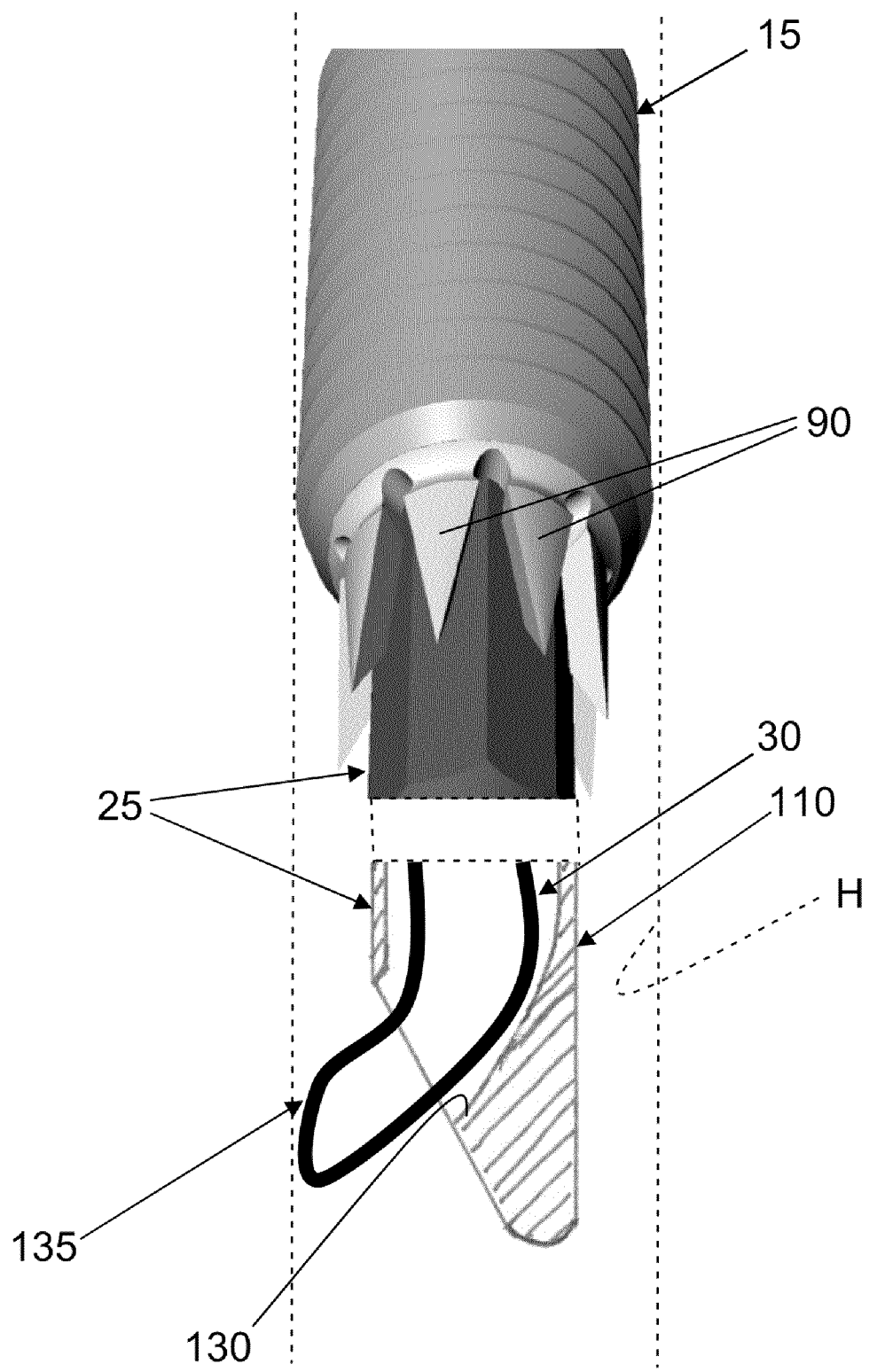
Figure 10:
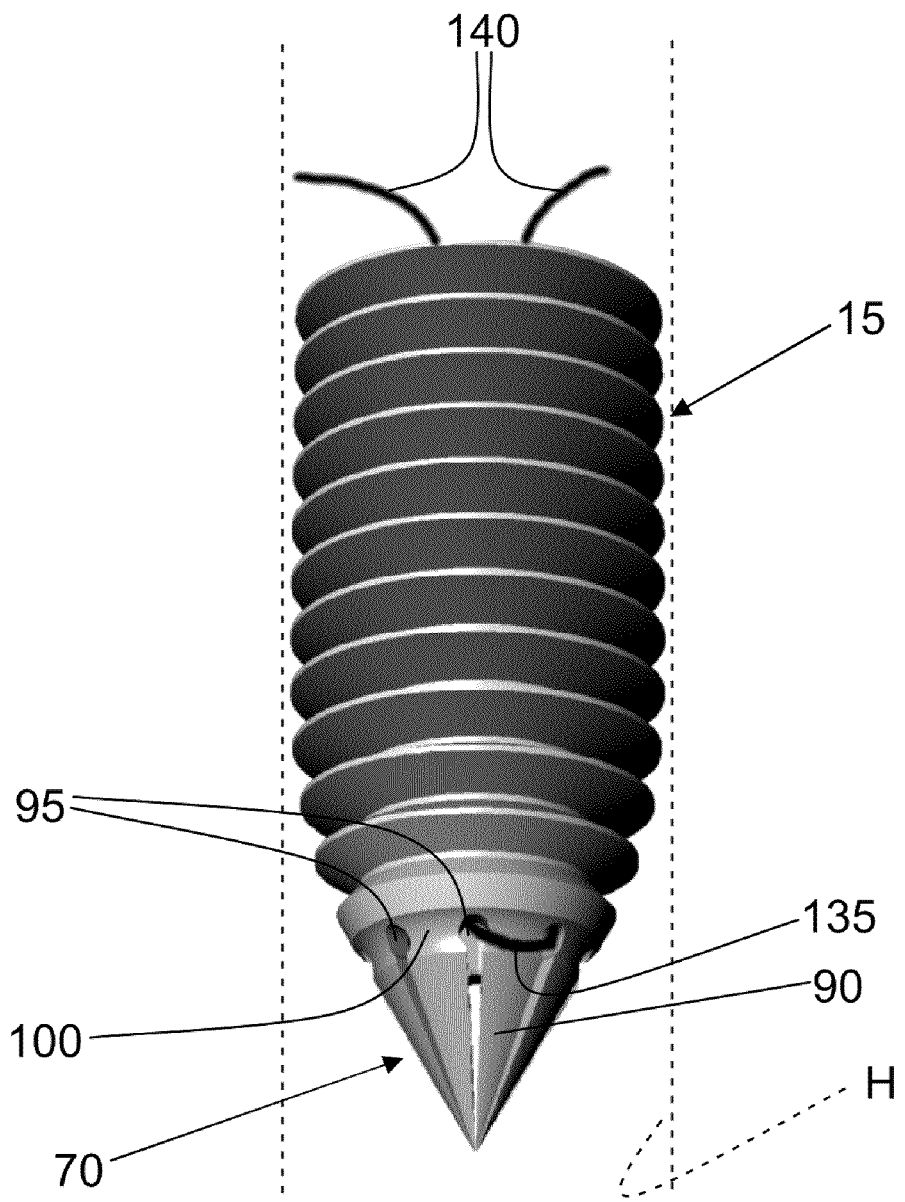

A hollow nose cone 70 is secured to distal end 50 of cylindrical body 45. Hollow nose cone 70 comprises a generally conical shape, with its base 75 being secured to distal end 50 of body 45 and with its pointed tip 80 extending distally away from body 45. The hollow interior of hollow nose cone 70 communicates with the distal end of bore 65 formed in body 45 of anchor 15. Hollow nose cone 70 also comprises a plurality of slits 85 which divide hollow nose cone 70 into a plurality of fingers 90. Slits 85 terminate, at their proximal ends, in enlarged circular openings 95. Preferably a circumferential surface groove 100 is formed in the outer surface of hollow nose cone 70, with circumferential surface groove 100 being aligned with, and communicating with, enlarged circular openings 95. Fingers 90 of nose cone 70 are formed out of a resilient material, such that (i) the distal ends of fingers 90 normally reside in a converging position, so as to collectively form pointed tip 80 of hollow nose cone 70, and (ii) the distal ends of fingers 90 can be forced radially outwardly, in the manner shown in FIG. 9, as will hereinafter be discussed in further detail.

Looking next at FIG. 1, driver 20 is a conventional torque driver. More particularly, driver 20 comprises a shaft 105 having a non-circular (e.g., hexagonal) cross-section. The non-circular cross-section of driver 20 corresponds to the non-circular bore 65 formed in anchor 15, in order that driver 20 may be engaged in bore 65 and used to turn anchor 15, as will hereinafter be discussed in further detail.

Figure 4:
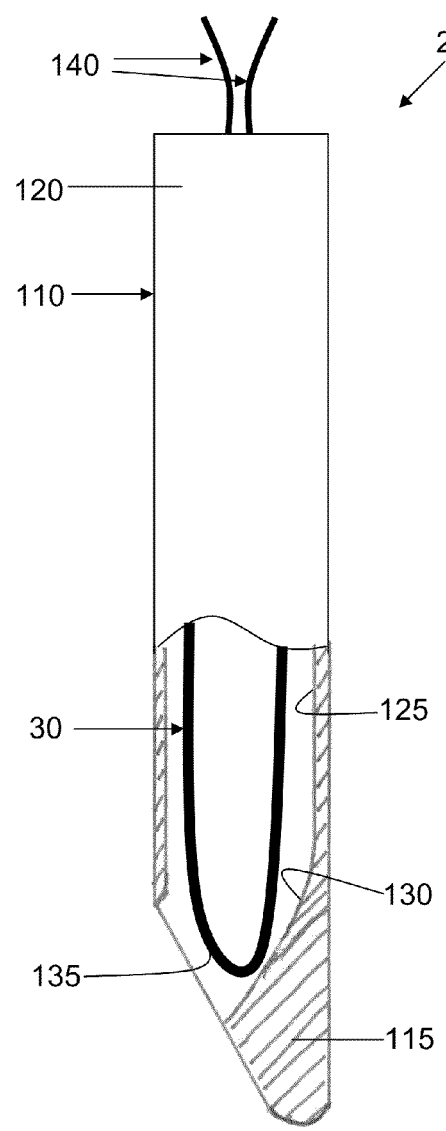
FIGS. 4 and 5 are schematic views showing the suture threader of the system of FIG. 1.
Figure 5:
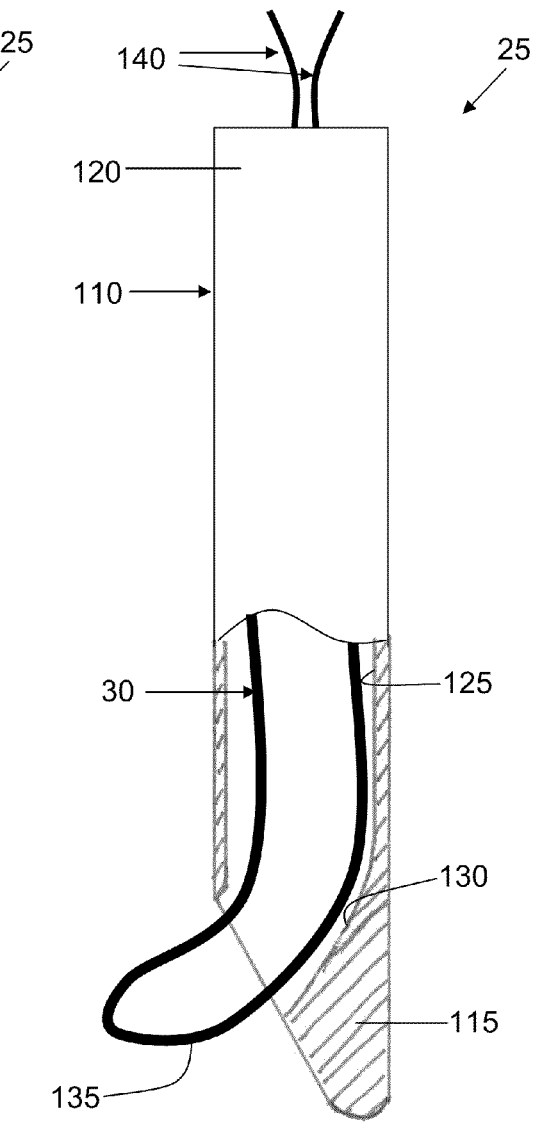

Looking next at FIGS. 1, 4 and 5, suture threader 25 generally comprises a shaft 110 having a distal end 115 and a proximal end 120. A lumen 125 extends along the length of shaft 110. Adjacent to distal end 115 of shaft 110, the side wall of lumen 125 preferably extends transverse to the longitudinal axis of shaft 110, e.g., as shown at 130. Transverse surface 130 serves to direct a loop of suture passing down lumen 125 transversely out of the distal end of shaft 110 when the suture encounters transverse surface 130.

More particularly, and still looking now at FIGS. 1, 4 and 5, suture threader 25 is intended to carry a suture 30 within lumen 125 of the suture threader. Suture 30 is intended to be "doubled over" within lumen 125 so that its distal loop 135 sits just proximal to transverse surface 130, and so that its two free ends 140 emerge from the proximal end of the suture threader in the manner shown in FIG. 4. Suture 30 can remain in this position, with its distal loop 135 shielded within and carried by shaft 110, as suture threader 25 is moved about. When suture 30 is thereafter advanced further down lumen 125, engagement of distal loop 135 with transverse surface 130 causes distal loop 135 to be directed transversely out of the shaft, in the manner shown in FIG. 5, so that distal loop 135 no longer sits substantially coaxial with the longitudinal axis of shaft 110. Thus, engagement of distal loop 135 with transverse surface 130 causes the distal loop to project laterally out of the distal end of shaft 110, whereby distal loop 135 can be "slipped over" a projecting finger 90 of anchor 15, as will hereinafter be discussed in further detail.

Looking next at FIGS. 6-10, anchor system 5 is preferably used in the following manner to attach suture to an anchor deployed in bone, whereby the anchor and suture may be used to attach soft tissue to bone.

Figure 6:
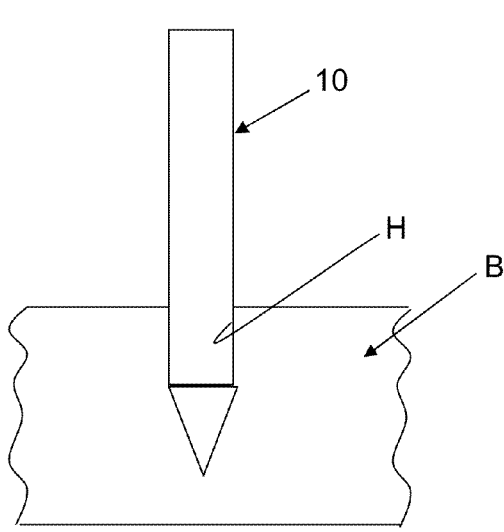
FIGS. 6-10 are schematic views showing a method of using the system of FIG. 1.

First, pilot drill 10 is used to form a pilot hole H in bone B (FIG. 6). Alternatively, hole H may be made by other means well known in the art, e.g., a sharp punch rod.

Figure 7:
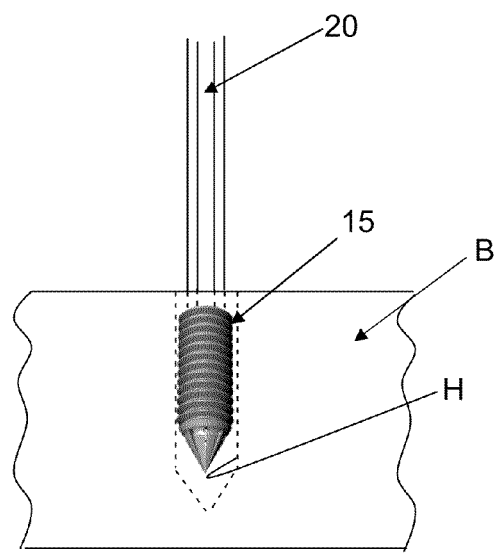
Figure 8:
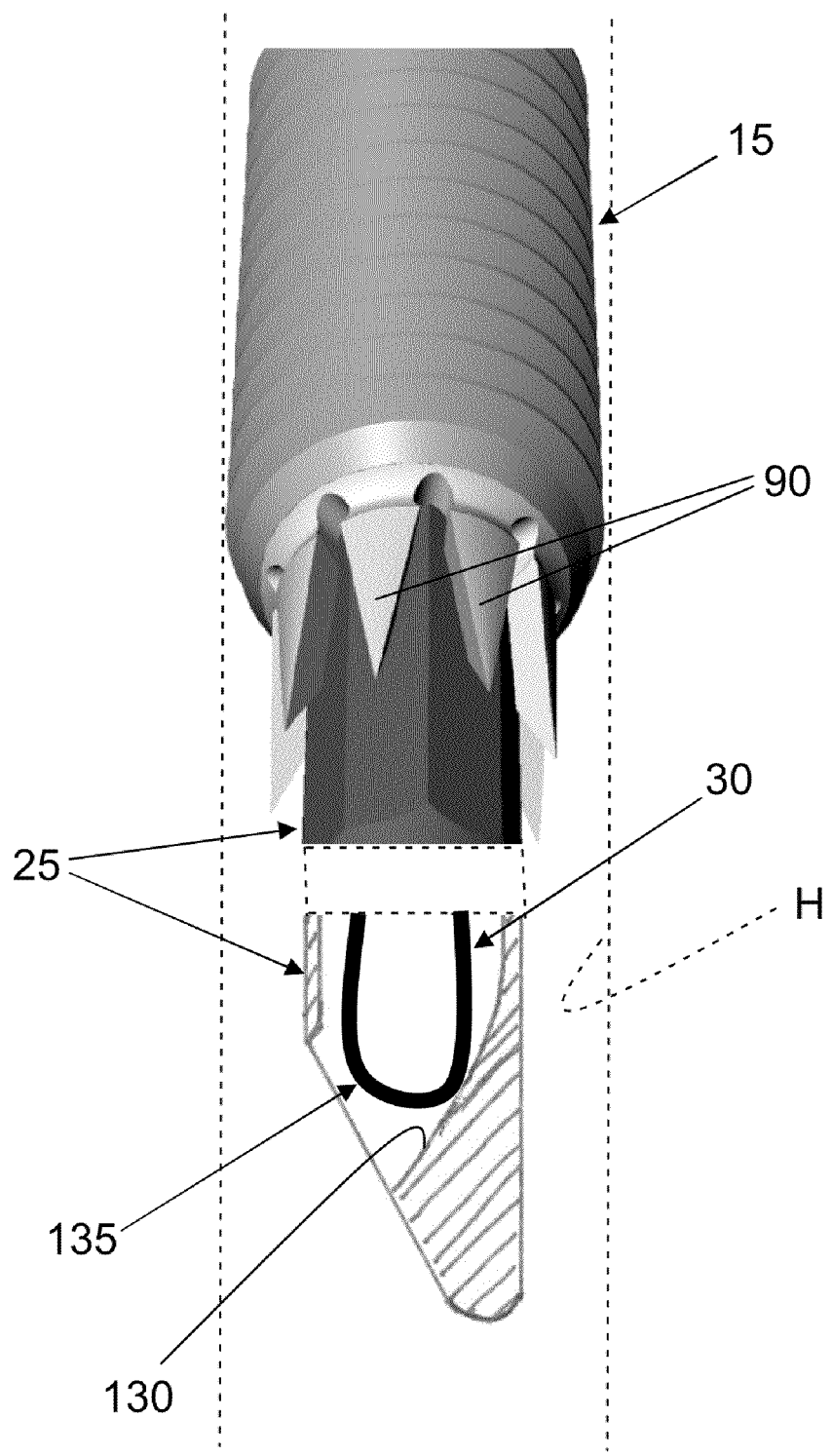

Next, driver 20 is used to screw anchor 15 into hole H in bone B (FIG. 7). More particularly, driver 20 is inserted into bore 65 of anchor 15, and then driver 20 is used to turn anchor 15 into hole H. It should be appreciated that, as this occurs, driver 20 is inserted only a portion of the way down bore 65 in anchor 15, so that driver 20 does not enter hollow nose cone 70 of anchor 15 and so that fingers 90 of hollow nose cone 70 remain in their closed position (i.e., in the position shown in FIG. 2). After anchor 15 has been advanced an appropriate distance into hole H, driver 20 is withdrawn from anchor 15.

Next, suture threader 25 is used to attach a suture 30 to anchor 15 while the anchor is disposed in bone hole H. More particularly, suture 30 is positioned within suture threader 25 in the manner shown in FIG. 4, i.e., so that distal loop 135 of suture 30 is disposed just proximal to transverse surface 130, then suture threader 25 is advanced down bone hole H and down bore 65 of anchor 15 until the distal end of suture threader 25 extends through hollow nose cone 70 and spreads fingers 90 open (FIG. 8), then suture 30 is advanced distally within lumen 125 until distal loop 135 engages transverse surface 130 and is projected laterally out of the side of shaft 110 of suture threader 25 (FIG. 9), and then suture threader 25 is withdrawn proximally. As suture threader 25 is withdrawn proximally, the laterally-projecting distal loop 135 of suture 30 is snared by one of the projecting fingers 90 of anchor 15. Further proximal movement of suture threader 25 allows resilient fingers 90 of nose cone 70 to close, thereby locking distal loop 135 of suture 30 over a finger 90, with distal loop 135 settling into circumferential surface groove 100 between two enlarged circular openings 95, in the manner shown in FIG. 10.

If desired, suture threader 25 can be configured so as to have a shaft 110 with a circular cross-section. More preferably, however, shaft 110 is provided with a cross-section which matches the cross-section of bore 65 in anchor 15, so that the angular disposition of suture threader 25 is coordinated with the angular disposition of anchor 15, whereby to facilitate alignment of distal loop 135 of suture 30 with a finger 90 of anchor 15. This arrangement helps ensure that distal loop 135 of suture 30 engages a finger 90 of anchor 15 during retraction of the suture threader from the anchor.

Significantly, if desired, additional sutures 30 may be attached to anchor 15 deployed in bone hole H, either on the same finger 90 or on a different finger 90, by repeating the foregoing procedure.

Thus it will be seen that suture anchor system 5 permits one or more sutures 30 to be attached to anchor 15 after the anchor has been deployed in bone B. This is a significant advance in the art, since conventional suture anchors require that the suture be attached to the suture anchor before the anchor is deployed in bone, thereby "freezing" the anchor/suture configuration prior to deployment of the anchor in the bone. Contrastingly, with the novel suture anchor system 5 of the present invention, the surgeon can deploy the anchor in the bone and then attach one or more sutures to the anchor, as the surgeon desires, thereby permitting the surgeon to vary the anchor/suture configuration at any time during the procedure, including after the anchor has been deployed in the bone. Thus, the surgeon can decide, mid-procedure, on the number of sutures to be attached to the anchor.

Furthermore, where multiple anchors 15 are deployed in bone, the present invention permits a single suture 30 to be attached to multiple anchors.

Additionally, a repair construct can be formed using one or more anchors 15 combined with other, dissimilar anchors of the sort known in the art.

Thus it will be seen that the present invention permits the surgeon to utilize a plurality of sutures and a plurality of anchors in a procedure and to determine, mid-procedure, precisely which sutures are to be attached to precisely which anchors.

In addition to the foregoing, as a consequence of the ability of the present invention to permit suture to be attached to the anchor after the anchor has been deployed in the bone, the suture can be attached to the soft tissue either before the suture is attached to the anchor or after the suture has been attached to the anchor.

Figure 37:
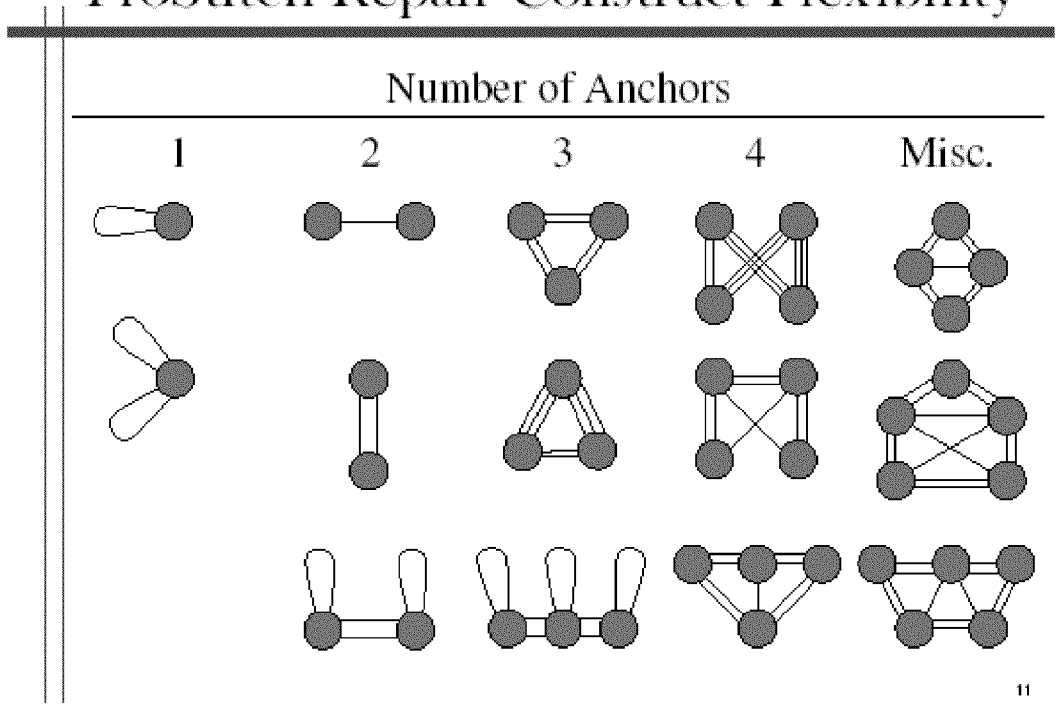
FIG. 37 illustrates examples of various stitching patterns which may be used to capture suture to an anchor.
Figure 38:
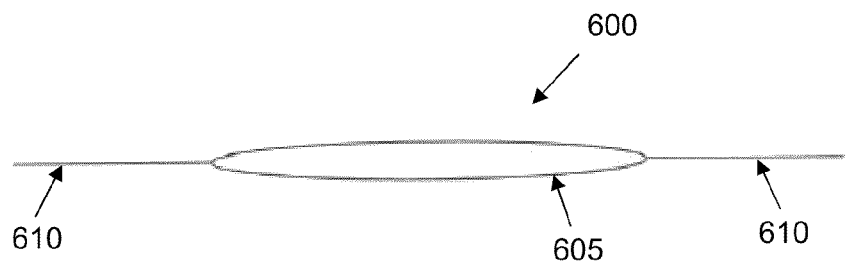
FIGS. 38-44 are schematic views illustrating suture designs which may be used in accordance with the present invention.
Figure 39:
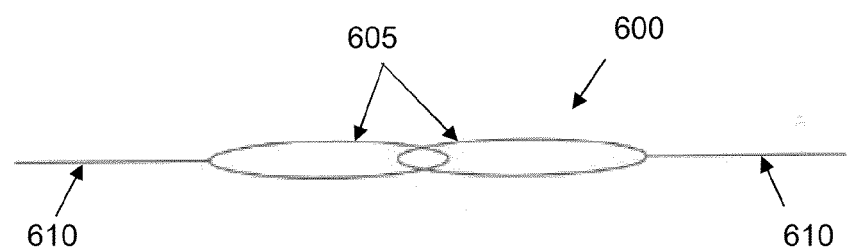

Thus, the present invention provides the surgeon with tremendous flexibility when attaching soft tissue to bone, since it effectively allows the surgeon to treat the anchor and the one or more sutures as separate components which may be married at any stage in the procedure, and with the ultimate anchor/suture configuration being variable at any stage in the procedure. This has not heretofore been possible with the suture anchors of the prior art. See, for example, FIG. 37 which shows just some of the many stitching patterns which may be created by passing one stitch through one anchor, one stitch through multiple anchors, multiple stitches through one anchor or multiple stitches through multiple anchors.

Figure 11:
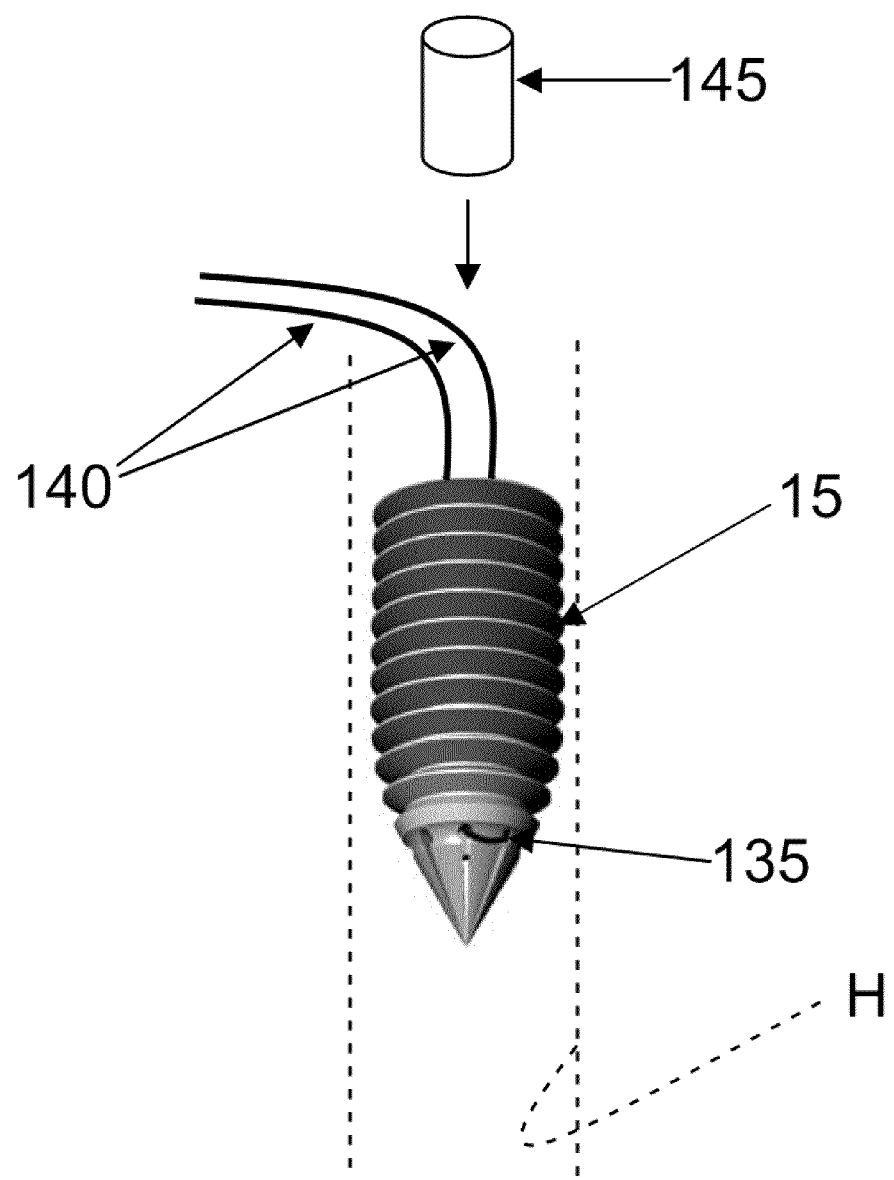
FIG. 11 is a schematic view of a suture-binding plug which may be used with the anchor shown in FIGS. 2 and 3.

Significantly, suture anchor system 5 also permits knotless suture fixation to be effected. More particularly, and looking now at FIG. 11, after one or more sutures 30 have been attached to soft tissue and also attached to an anchor, and the sutures appropriately cinched, a plug 145 may be forced down into the proximal end of bore 65 of the anchor, whereby to make an interference fit between plug 145 and anchor 15 and immovably capture suture 30 to anchor 15. Thus, suture anchor system 5 permits knotless suture fixation to be achieved. This is a significant advance over prior art suture anchors.

Figure 12:
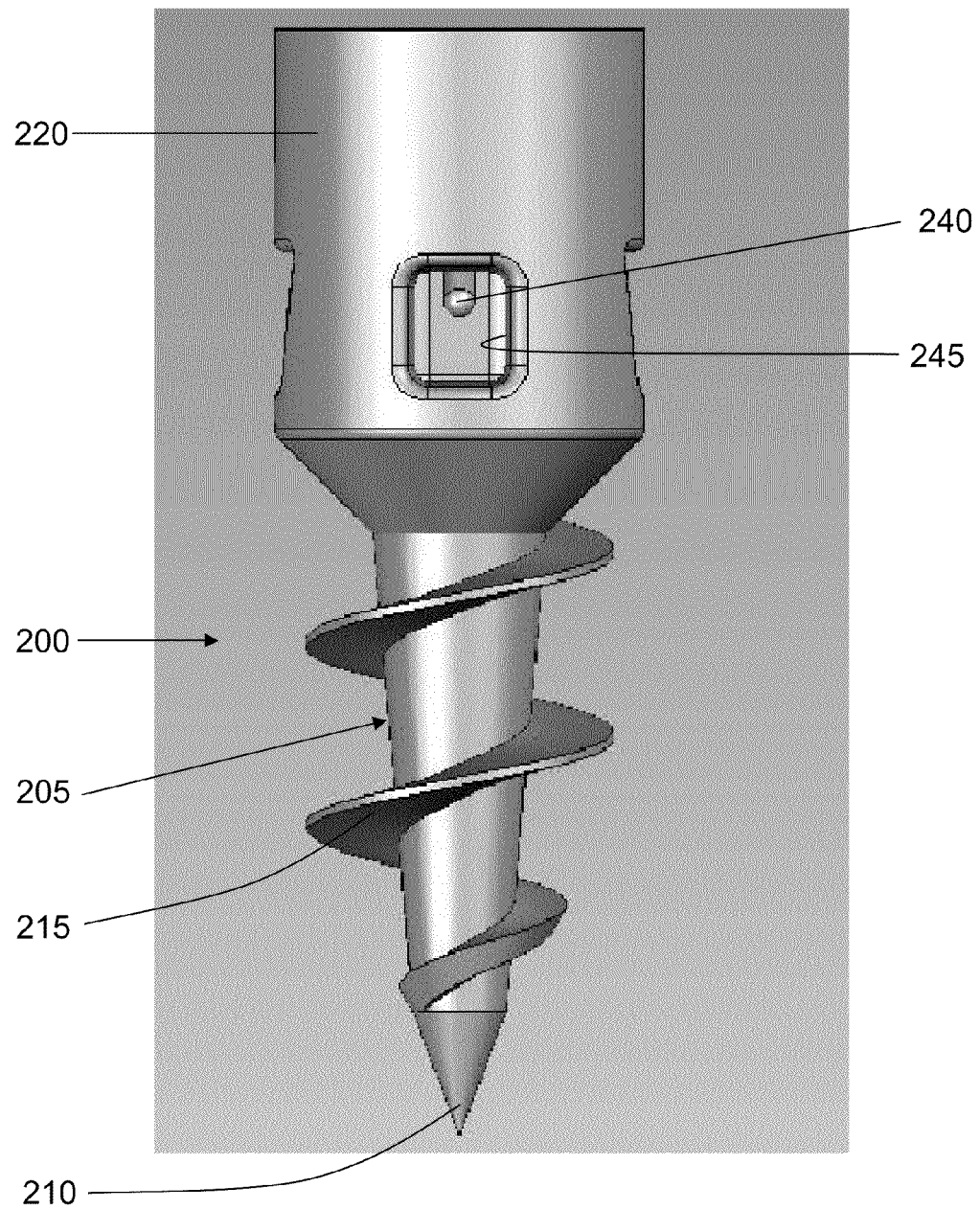
FIGS. 12-14 are schematic views of another anchor formed in accordance with the present invention.
Figure 13:
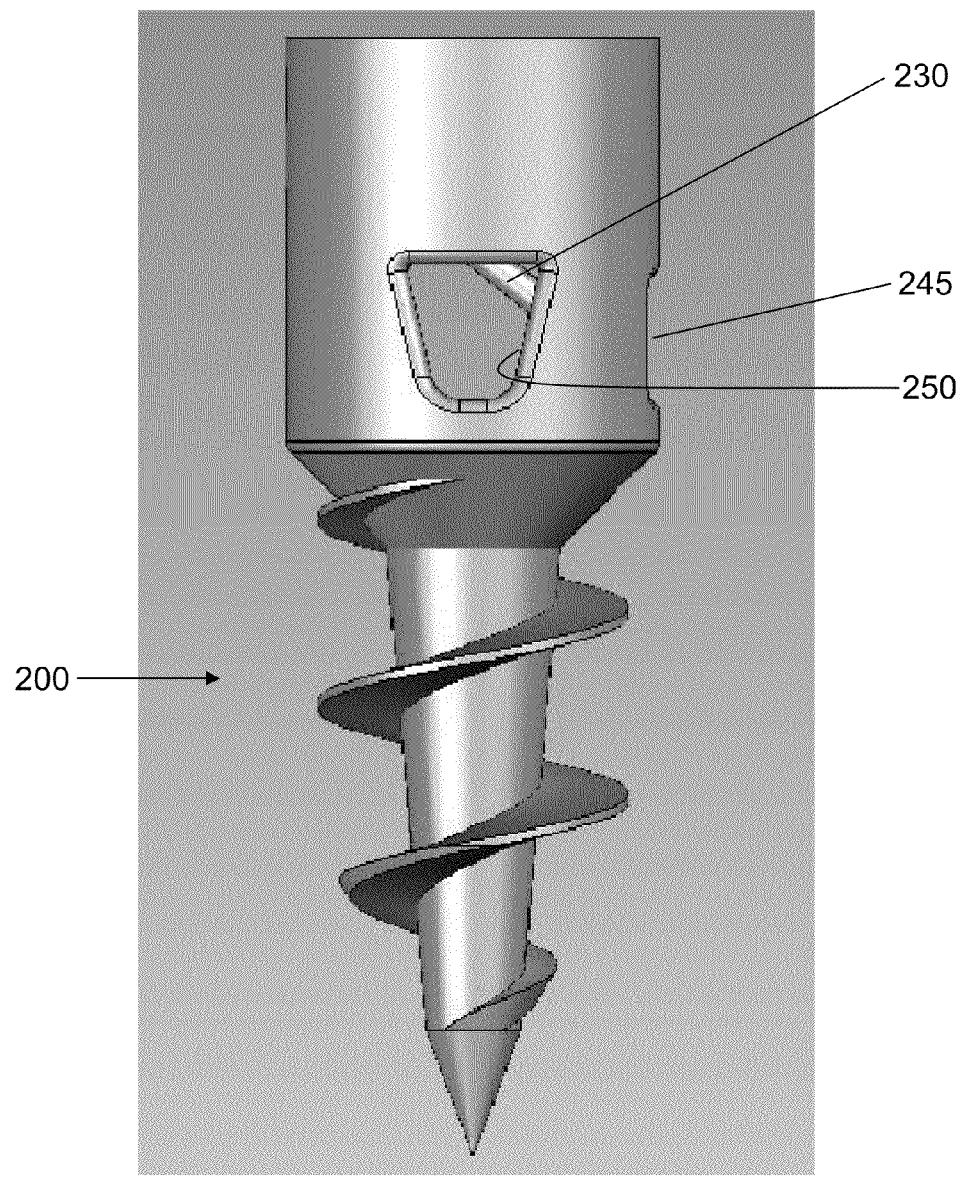
Figure 14:
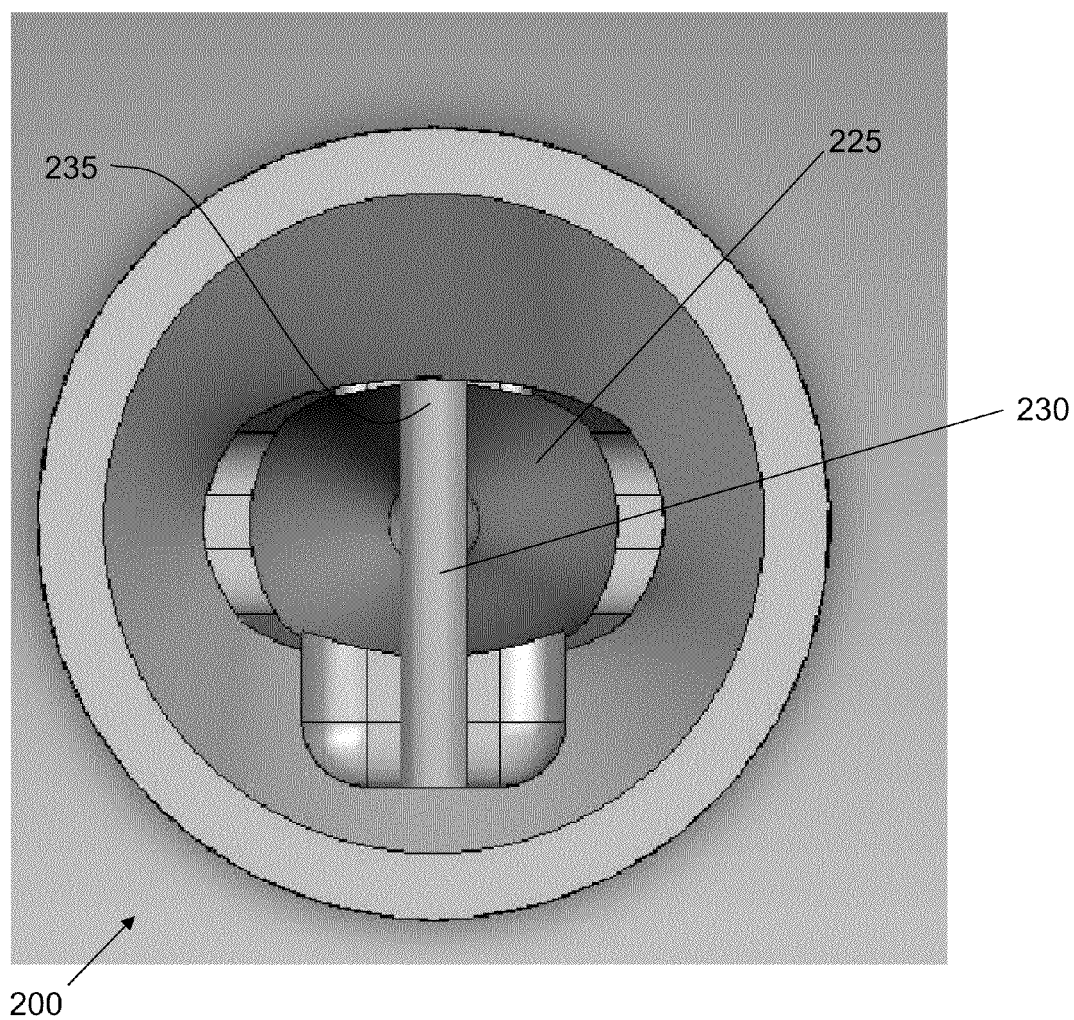

Looking next at FIGS. 12-14, there is shown another anchor 200 also formed in accordance with the present invention. Anchor 200 generally comprises a shaft 205 terminating in a pointed tip 210 and having screw threads 215 thereon. Anchor 200 also comprises a head 220 having an axial recess 225 formed therein. Axial recess 225 has a non-circular (e.g., ovoid) cross-section. A flexible crossbar 230 extends across axial recess 225. More particularly, a flexible crossbar 230 comprises a fixed end 235 which is secured to head 220 and a free end 240, whereby to form a cantilever construction. Flexible crossbar 230 extends at a transverse angle to the longitudinal axis of anchor 200. More particularly, flexible crossbar 230 descends distally as it extends across axial recess 225, in the manner shown in FIGS. 13 and 14, so that flexible crossbar 230 has its free end 240 disposed distally of its opposing fixed end 235. Head 220 of anchor 15 also comprises a crossbar window 245. The free end of flexible crossbar 230 extends into crossbar window 245 for reasons which will hereinafter be discussed. Head 220 also comprises a pair of diametrically-opposed side windows 250.

Figure 15:
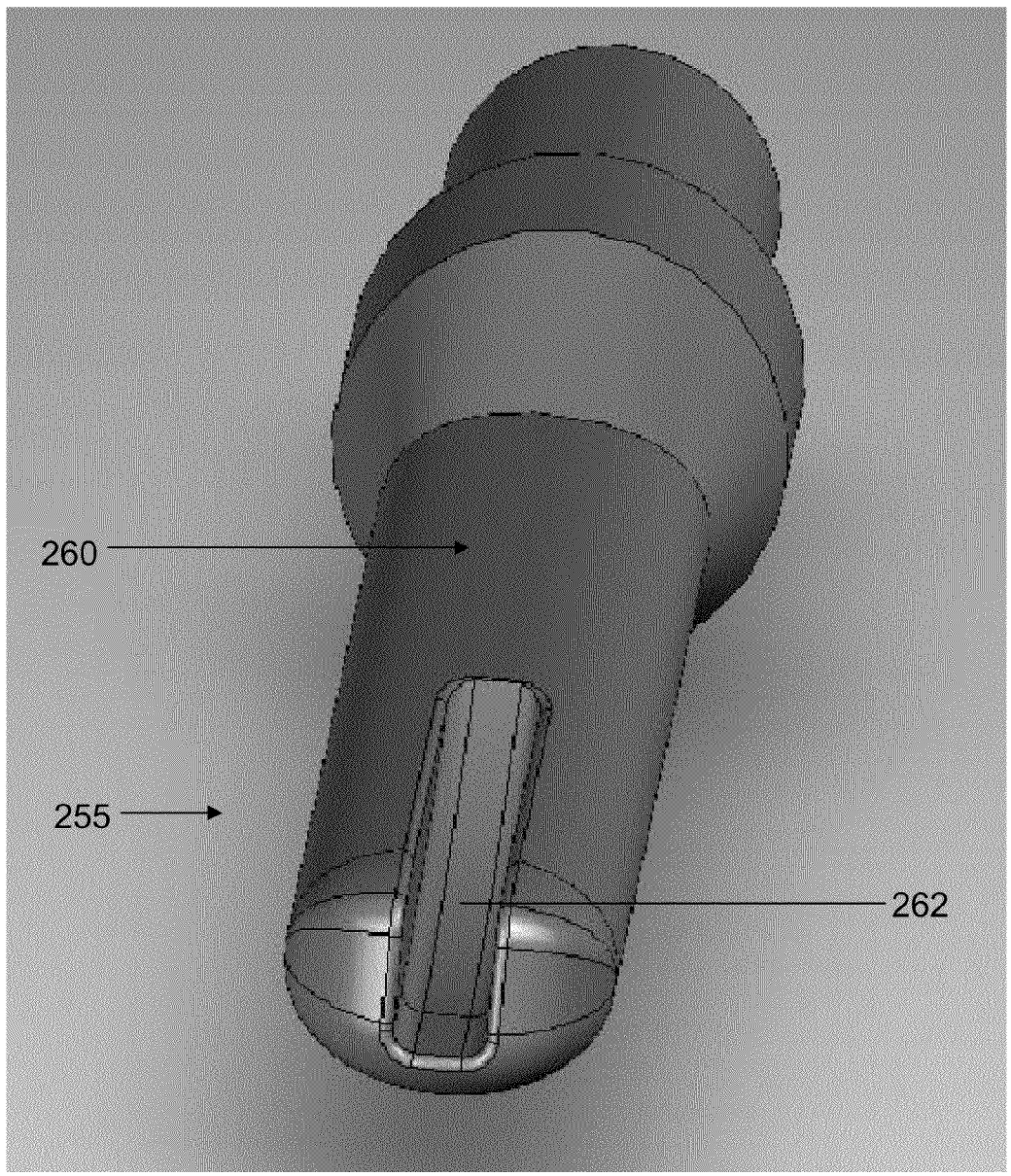
FIGS. 15 and 16 are schematic views of a driver which may be used to insert the anchor of FIGS. 12-14 in a bone.
Figure 16:
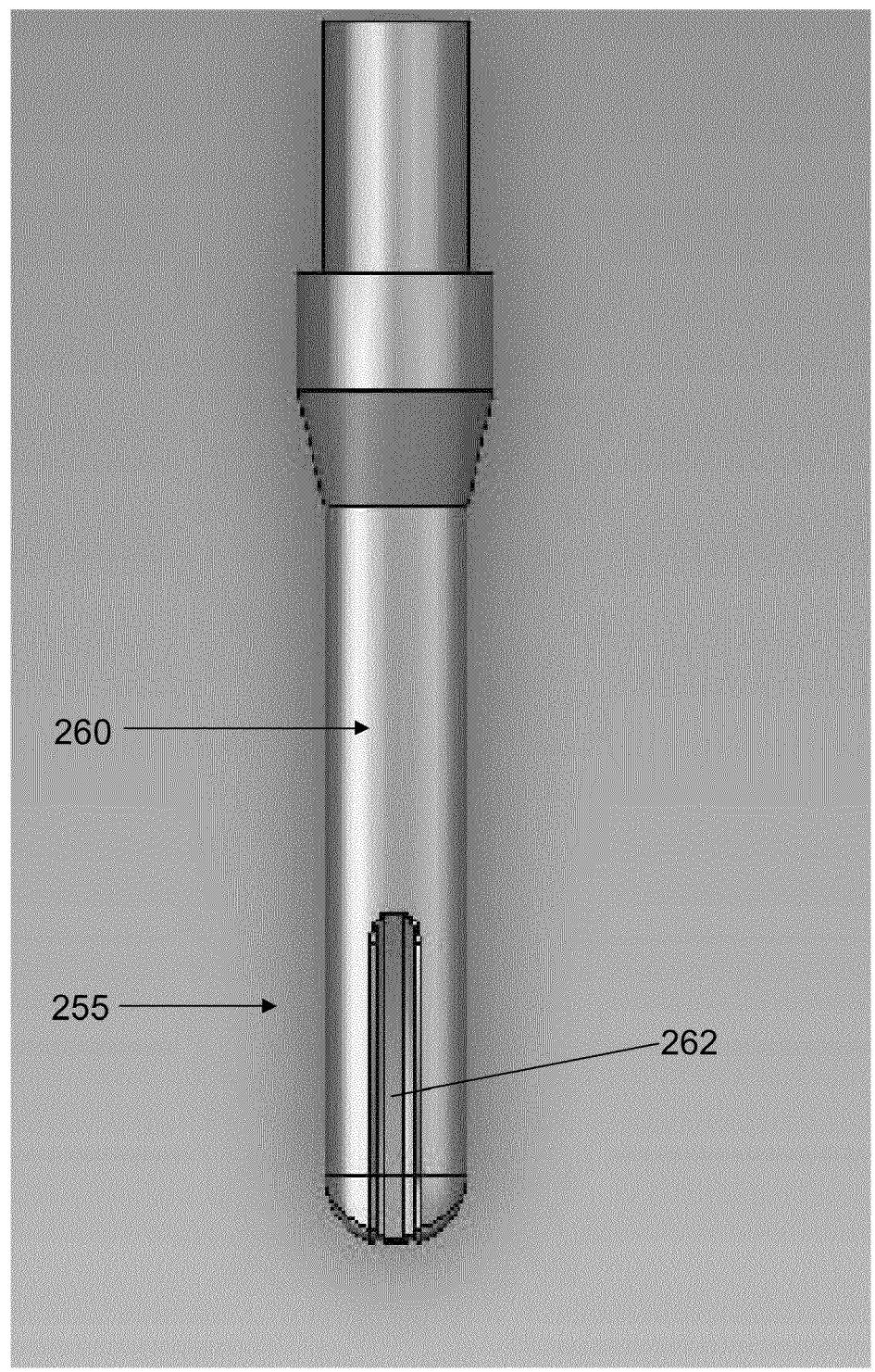

Anchor 200 is intended to be screwed into bone by a driver 255 (FIGS. 15 and 16). More particularly, driver 255 generally comprises a shaft 260 having a non-circular (e.g., ovoid) cross-section. The cross section of shaft 260 is coordinated with the cross-section of axial recess 225 in anchor 200 in order that driver 255 can be used to turn anchor 200, whereby to screw anchor 200 into bone. Driver 255 includes a slot 262 for accommodating flexible crossbar 230 of anchor 200, as will hereinafter be discussed in further detail.

Figure 17:
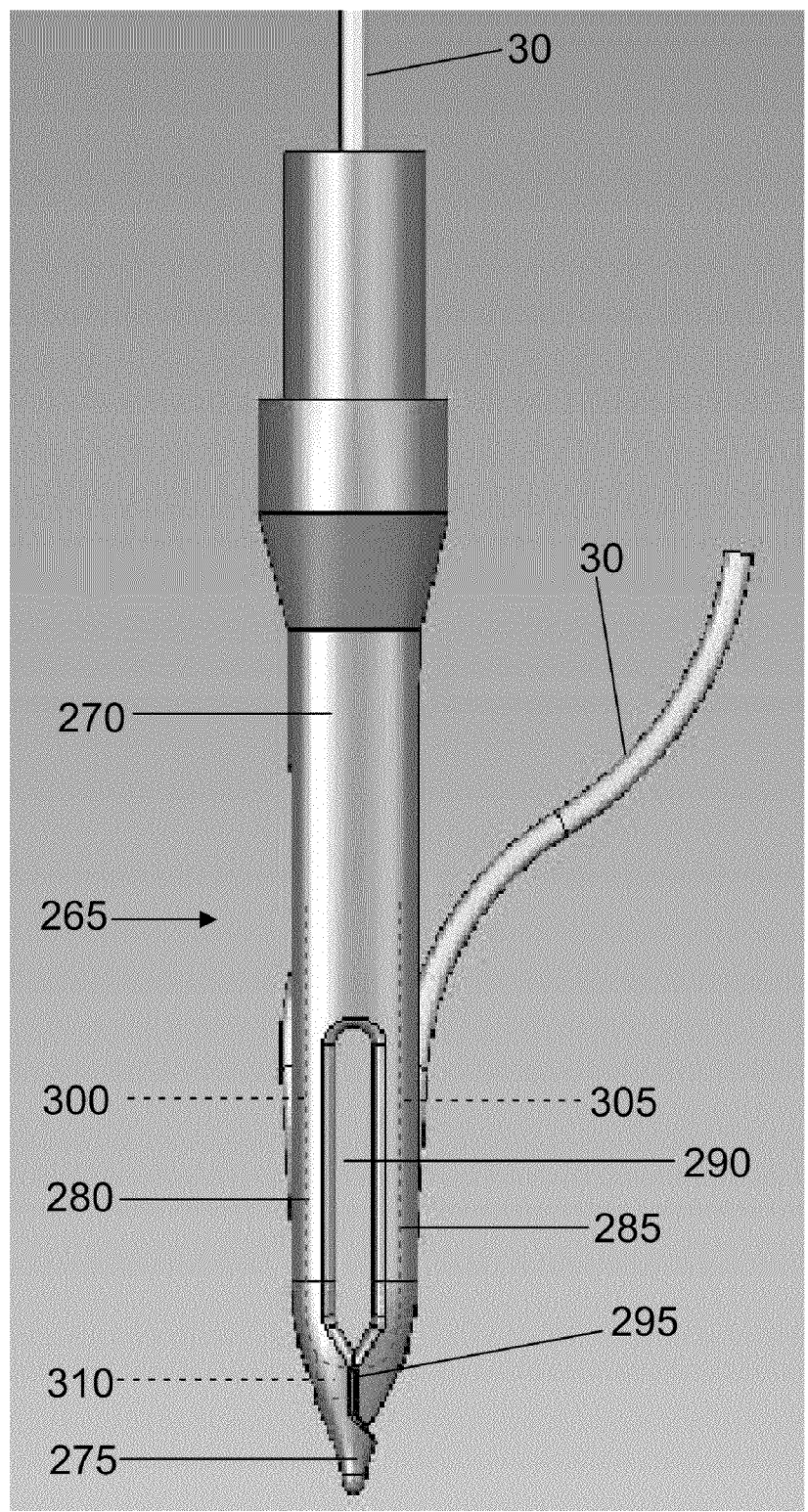
FIG. 17 is a schematic view of another suture threader which may be used in conjunction with the anchor of FIGS. 12-14.

Looking next at FIG. 17, there is shown a suture threader 265 which may be used in conjunction with anchor 200. Suture threader 265 generally comprises a shaft 270 terminating in a distal tip 275. Shaft 270 is cut along its distal end so as to produce a pair of parallel fingers 280, 285 which are separated intermediate their length by a window 290. Preferably fingers 280, 285 re-converge distal to window 290 at an interface 295. A surface groove 300 is formed in finger 280 for receiving suture 30. Another surface groove 305 is formed in finger 285 for receiving another portion of suture 30. An opening 310 in finger 280 permits suture 30 to pass from surface groove 300 to surface groove 305. It will be appreciated that suture 30 will be configured in the form of a distal loop in the region where suture 30 passes from surface groove 300, through opening 310 and into surface groove 305, as will hereinafter be discussed below. At least finger 285, and preferably finger 280 as well, is formed out of a resilient material, such that finger 280 can spring toward and away from finger 285.

Anchor 200, driver 255 and suture threader 265 are preferably used as follows. First, a pilot hole is preferably made in the bone which is to receive anchor 200, although in some circumstances the pilot hole may be omitted. Then driver 255 is used to screw anchor 200 into the bone. This is done by advancing the distal end of driver 255 into axial recess 225 of anchor 200, with flexible crossbar 230 received in slot 262 in driver 255, and then turning driver 255 so as to screw anchor 200 into the bone.

If desired, a suture may be looped around flexible crossbar 230 prior to engagement of the driver with the anchor, and then the two free ends of the suture held at the same time that the handle of the driver is grasped, whereby to ensure that the anchor is held to the driver as the anchor is introduced into the patient and then into the bone. The suture can thereafter be left attached to the anchor for use in a subsequent repair procedure or detached from the anchor and withdrawn from the surgical site.

Figure 18:
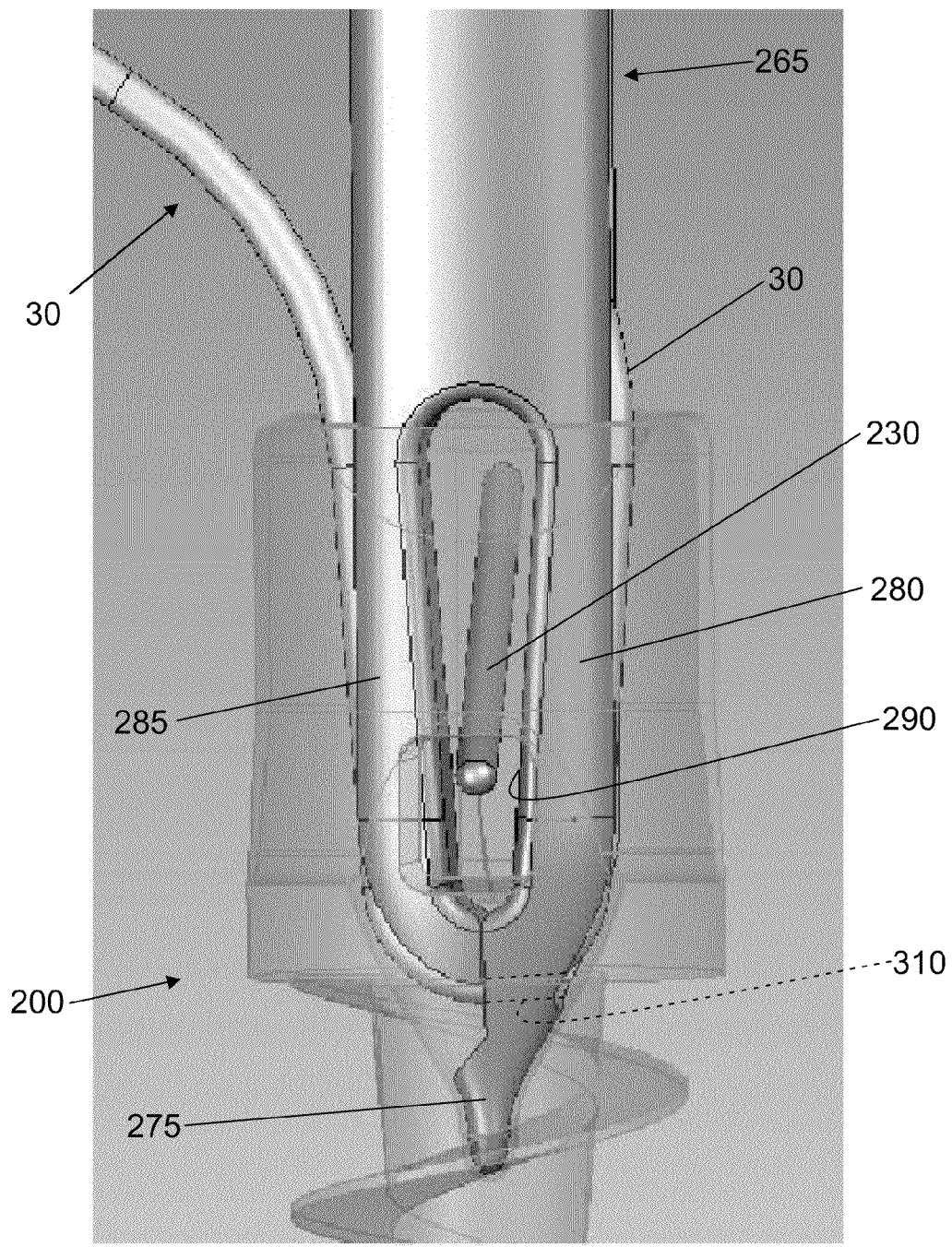
FIGS. 18-20 are schematic views showing a method of using the anchor of FIGS. 12-14 and the suture threader of FIG. 17.
Figure 19:
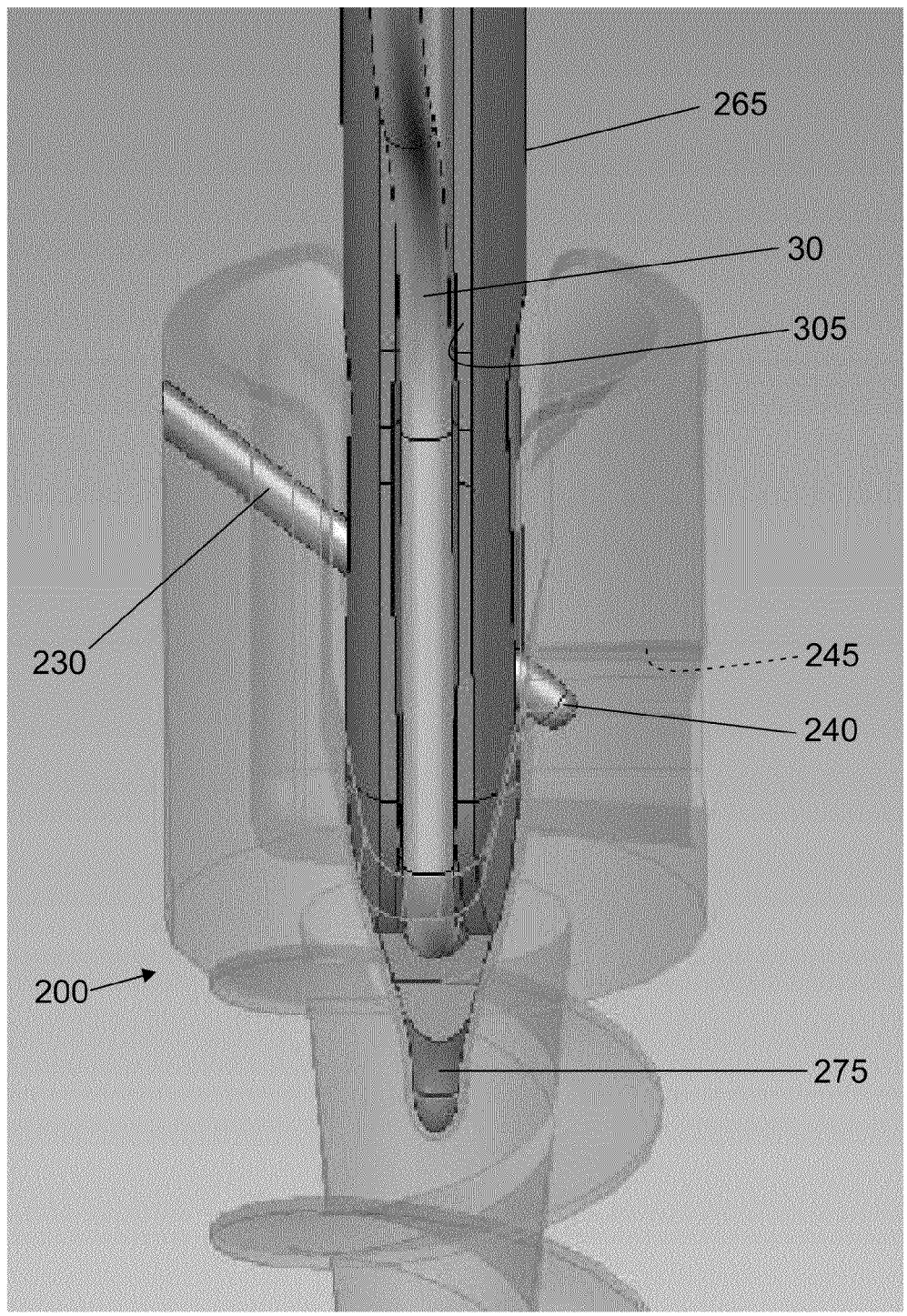
Figure 20:
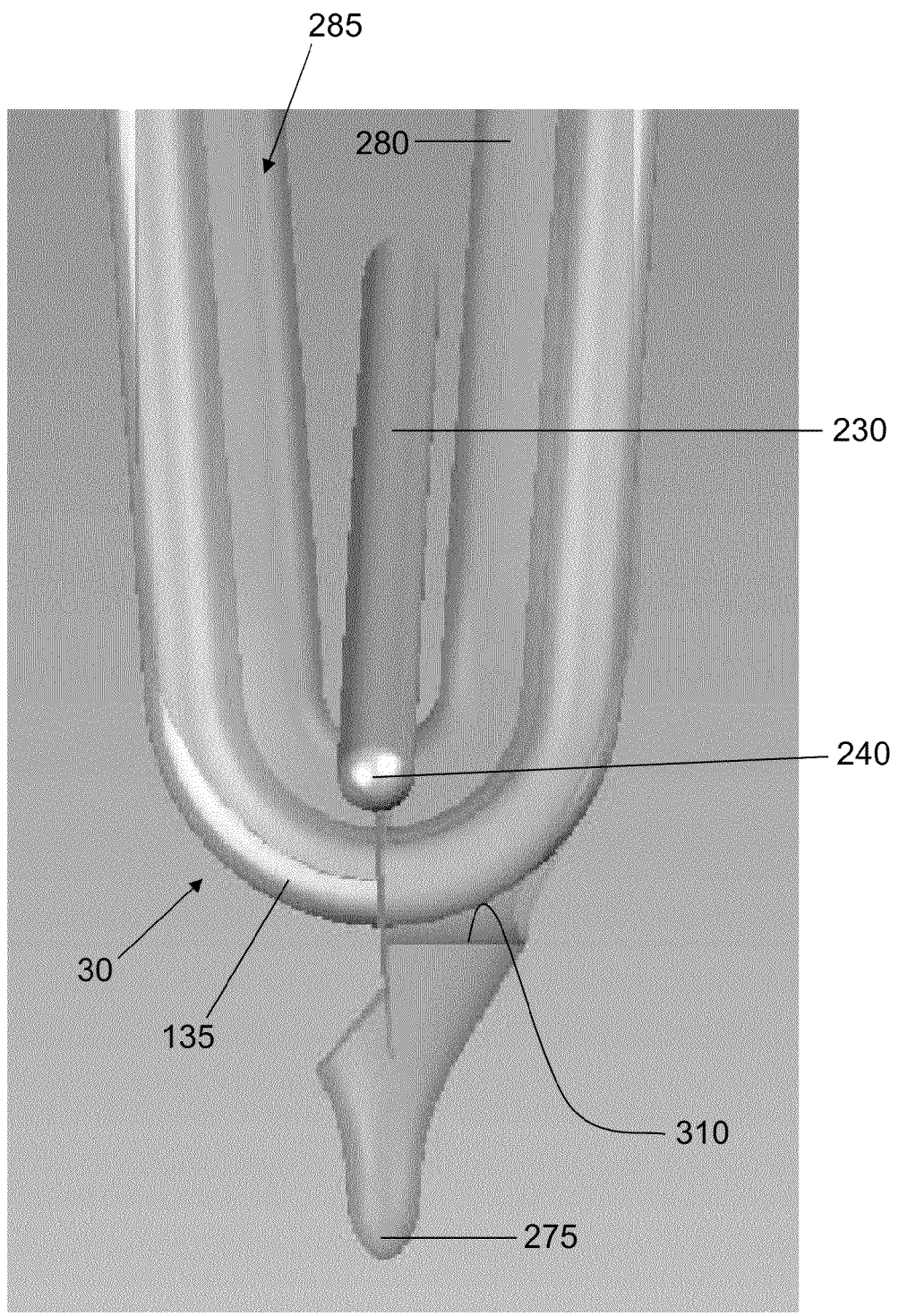

Next, suture threader 200, with suture 30 disposed thereon (i.e., seated within surface groove 300, opening 310 and surface groove 305), is advanced into axial recess 225 of anchor 200. As this occurs, and looking now at FIGS. 18-20, the distal end of suture threader 265 engages flexible crossbar 230 and, by virtue of this engagement, causes the free end of flexible crossbar 230 to flex downwardly, "skidding" along the exterior surface of suture threader 265, until the free end of flexible crossbar 230 "pops" through window 290. This action provides tactile feedback to the surgeon, confirming that flexible crossbar 230 is seated in window 290. Thereafter, suture threader 265 is withdrawn proximally from axial recess 225 of anchor 200. As this occurs, fingers 280 and 285 of suture threader 265 engage flexible crossbar 230, causing at least finger 285 to flex outward so as to permit flexible crossbar 230 to pass by the bifurcated fingers 280, 285. However, as this occurs, flexible crossbar 230 catches suture loop 135 formed at the distal end of suture 30, causing suture 30 to be captured on anchor 200. In this respect it should be appreciated that by configuring the anchor so that free end 240 of flexible crossbar 230 is normally disposed within crossbar window 245, any proximal motion of flexible crossbar 230 during retraction of suture threader 265 is limited by its engagement with the proximal surface of crossbar window 245, thereby ensuring that suture 30 remains engaged on flexible crossbar 230. Alternatively, if desired, crossbar window 245 can be replaced by another structure providing a transverse edge to limit proximal motion of flexible crossbar 230, e.g., a transverse bar.

Significantly, side windows 250 formed in anchor 200 permit fluids to pass from the interior of the bone through the anchor so as to reach the soft tissue being re-attached to the bone. This can be advantageous, since such fluids are frequently rich in growth-promoting factors which can expedite soft tissue regrowth.

The foregoing procedure may thereafter be repeated as desired so as to attach additional lengths of suture to the deployed anchor 200.

Thus it will be seen that anchor 200, driver 255 and suture threader 265 permit anchor 200 to be deployed in a bone and a suture to be thereafter attached to that anchor, so that soft tissue may be attached to the bone using the anchor and suture.

Figure 21:
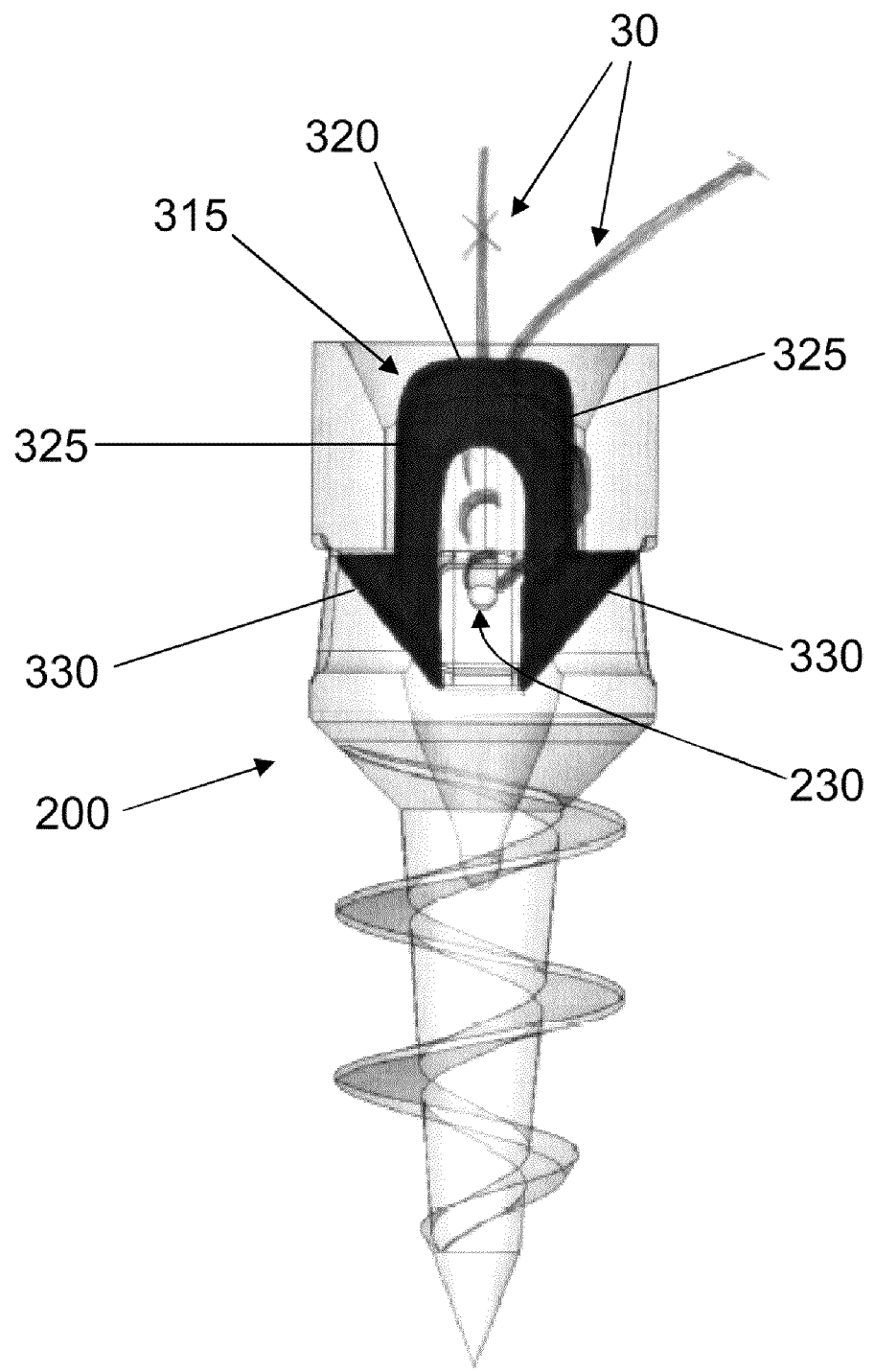
FIG. 21 is a schematic view of a suture-binding plug which may be used with the anchor of FIGS. 12-14.

If desired, and looking next at FIG. 21, a suture-binding plug may be inserted into the proximal end of anchor 200 so as to fix suture 30 relative to the anchor. More particularly, in this form of the invention, the plug may take the form of a cap 315 comprising a bridge portion 320 and a pair of descending legs 325 each terminating in a barb 330. Barbs 330 are intended to seat in side windows 250 of anchor 200, whereby to lock cap 315 to anchor 200, fixing suture 30 to anchor 200 in the process.

If desired, cap 315 can include a longitudinal bore for passing suture 30 therethrough. With this construction, cap 315 can be loaded onto the free ends of suture 30 and then slid down the suture and into position on the anchor. By interfacing cap 315 with the suture in this manner, cap 315 can be quickly and easily directed into its proper position without the risk of becoming a loose element within the body.

Figure 22:
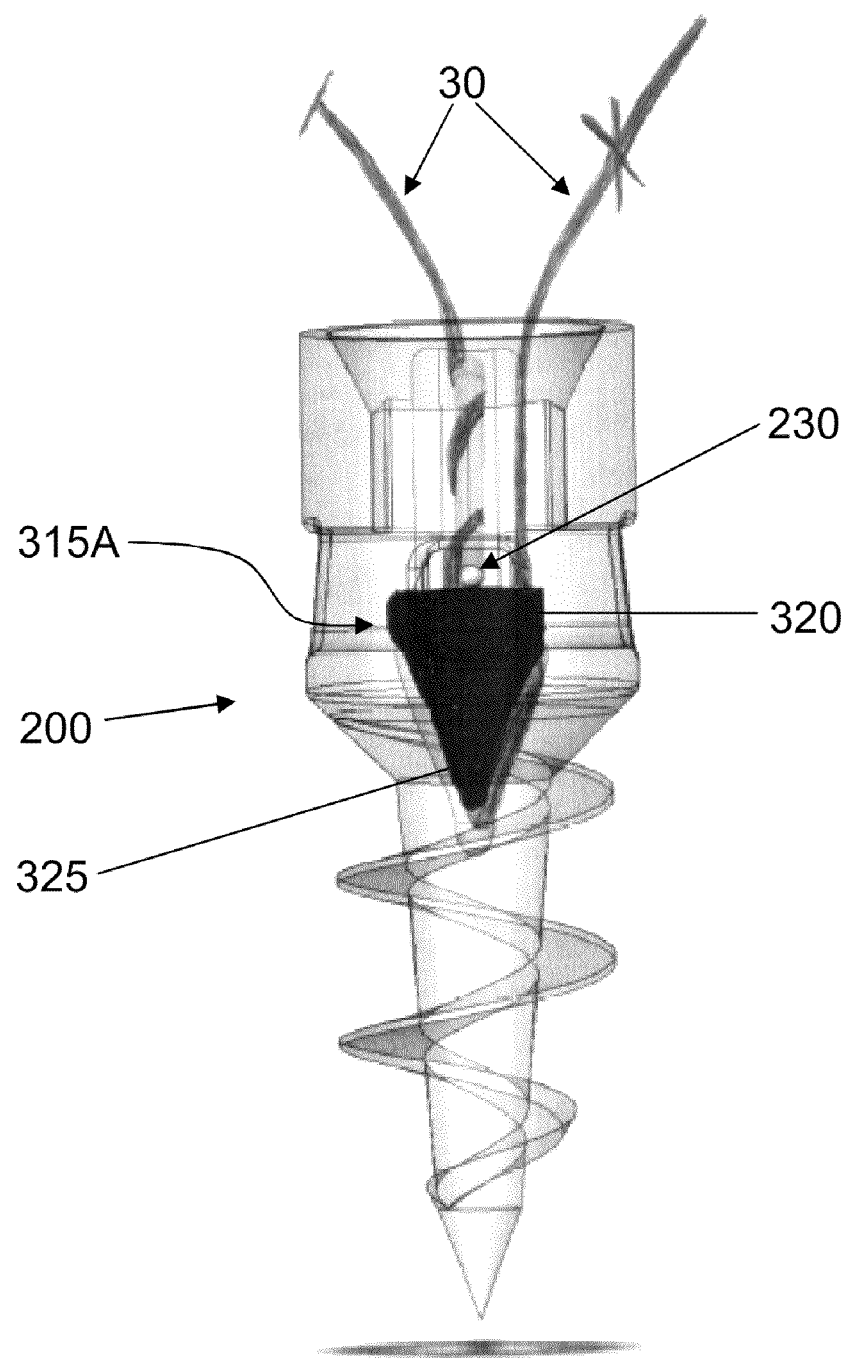
FIG. 22 is a schematic view of another suture-binding plug which may be used with the anchor of FIGS. 12-14.

Looking next at FIG. 22, the suture-binding plug may also take the form of a cap 315A which omits barbs 330, in which case legs 325 compress into a lower portion of axial recess 225, with flexible crossbar 230 securing bridge portion 320 to the anchor, and with bridge portion 320 securing suture 30 to the anchor.

Figure 23:
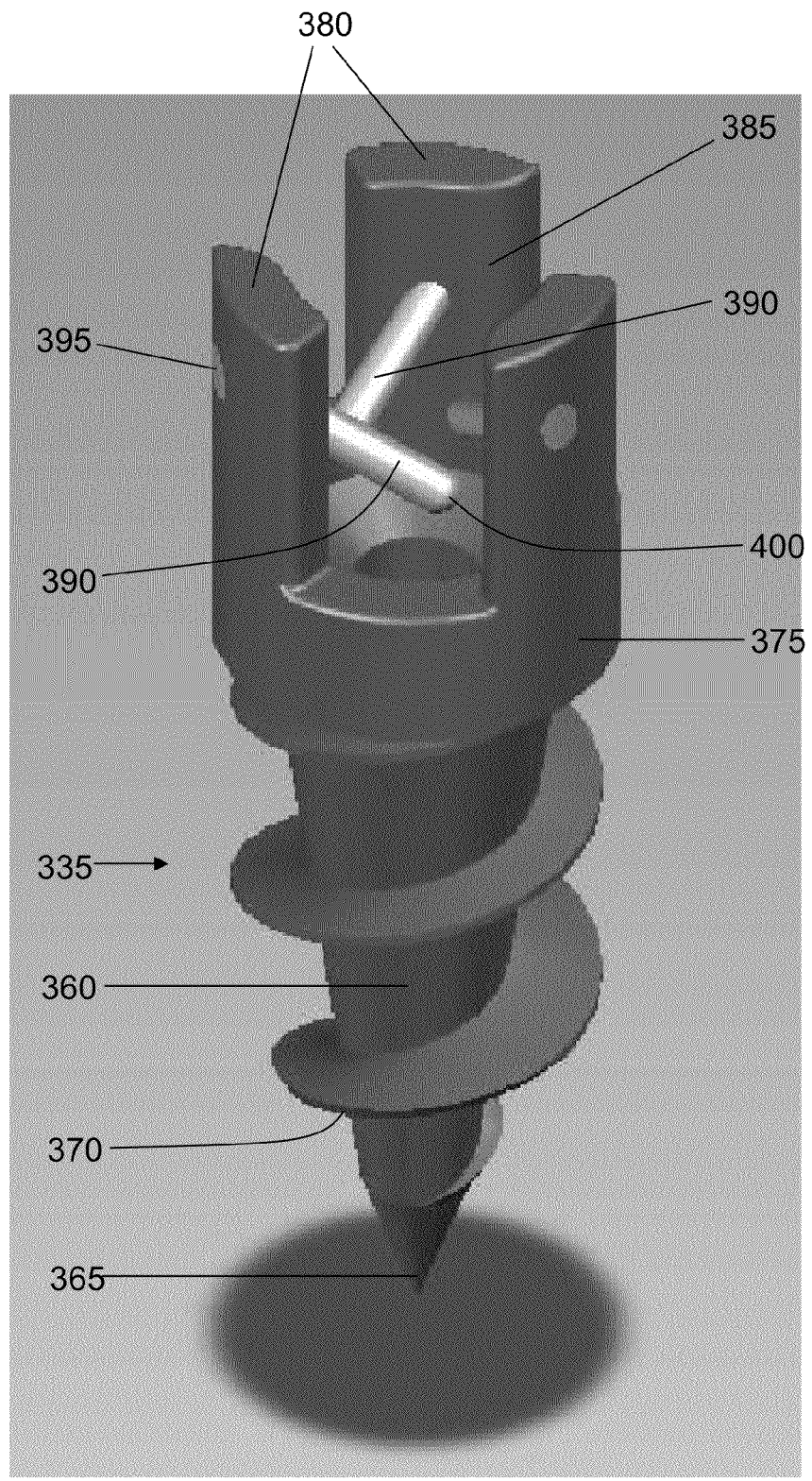
FIGS. 23 and 24 are schematic views of another anchor formed in accordance with the present invention.
Figure 24:
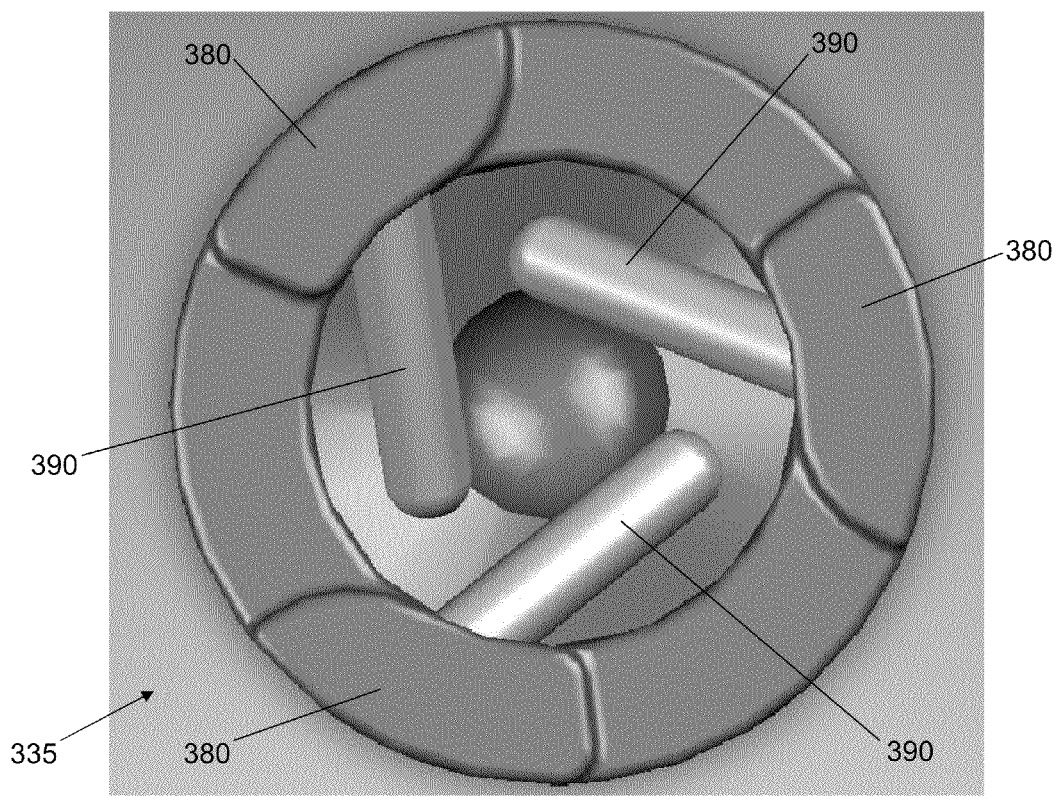

Looking next at FIGS. 23 and 24, there is shown still another anchor 335 formed in accordance with the present invention. Anchor 335 generally comprises a shaft 360 terminating in a pointed tip 365 and having screw threads 370 thereon. Anchor 335 also comprises a head 375, at least part of which is formed by a plurality of upstanding spaced elements 380, and having an axial recess 385 formed therein. Axial recess 385 can have a non-circular (e.g., ovoid) cross-section so that it can be turned with a driver having a shaft with a non-circular (e.g., ovoid) cross-section, whereby to turn anchor 200 into bone. Alternatively, anchor 200 can be turned by a driver having a distal end having a counterpart disposition to the plurality of upstanding spaced elements 380, whereby the driver can turn the anchor. A plurality of flexible crossbars 390 extend across axial recess 385. Flexible crossbars each comprise a fixed end 395 secured to anchor 335 and a free end 400, whereby to form a cantilever construction. Flexible crossbars 390 extend at a transverse angle to the longitudinal axis of anchor 335. More particularly, flexible crossbars 390 descend distally as they extend across axial recess 385, in the manner shown in FIG. 23, so that flexible crossbars 390 have their free ends 400 disposed distally of their opposing fixed ends 395.

Figure 25:
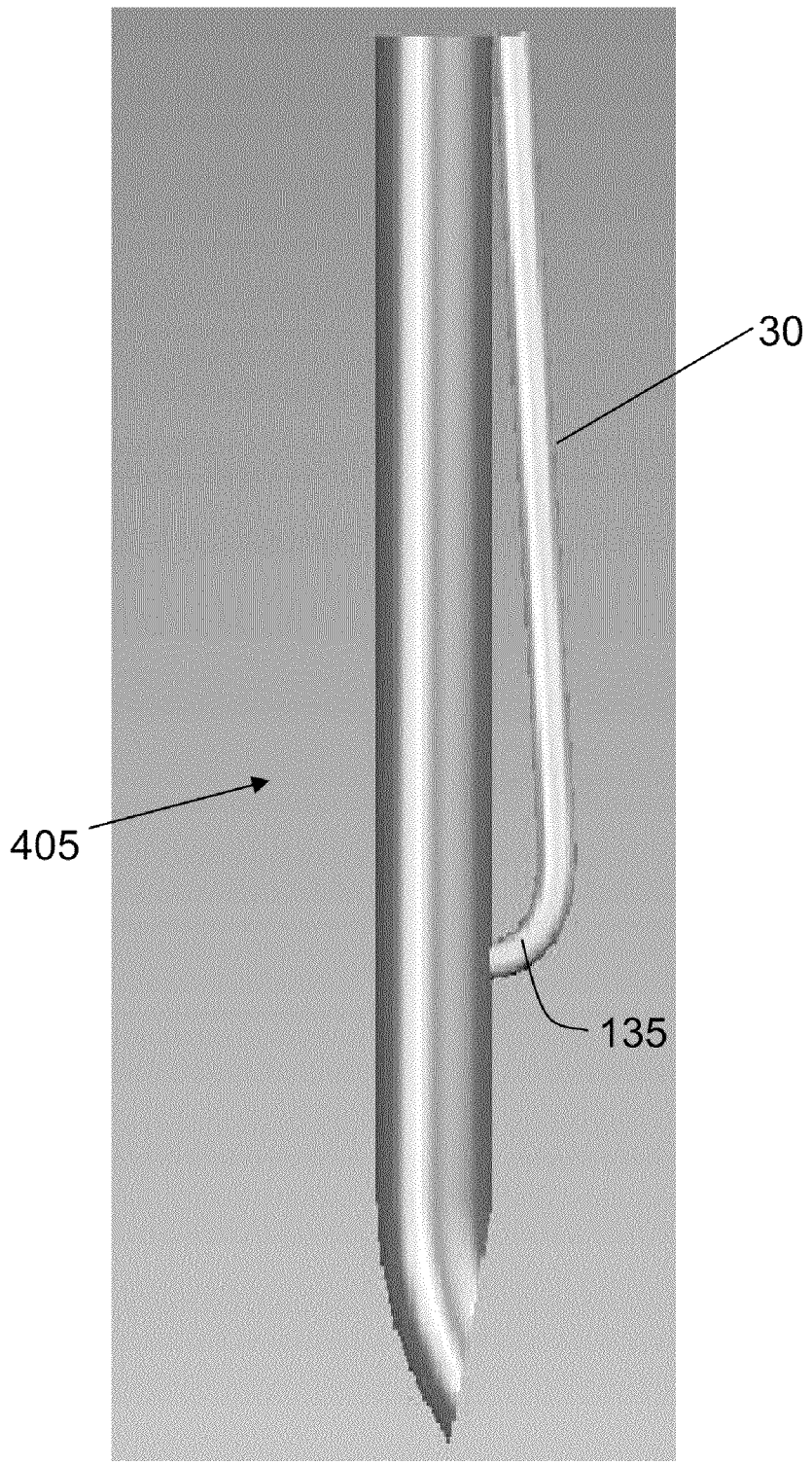
FIGS. 25 and 26 are schematic views of another suture threader which may be used in conjunction with the anchor of FIGS. 23 and 24.
Figures 26, 26A:
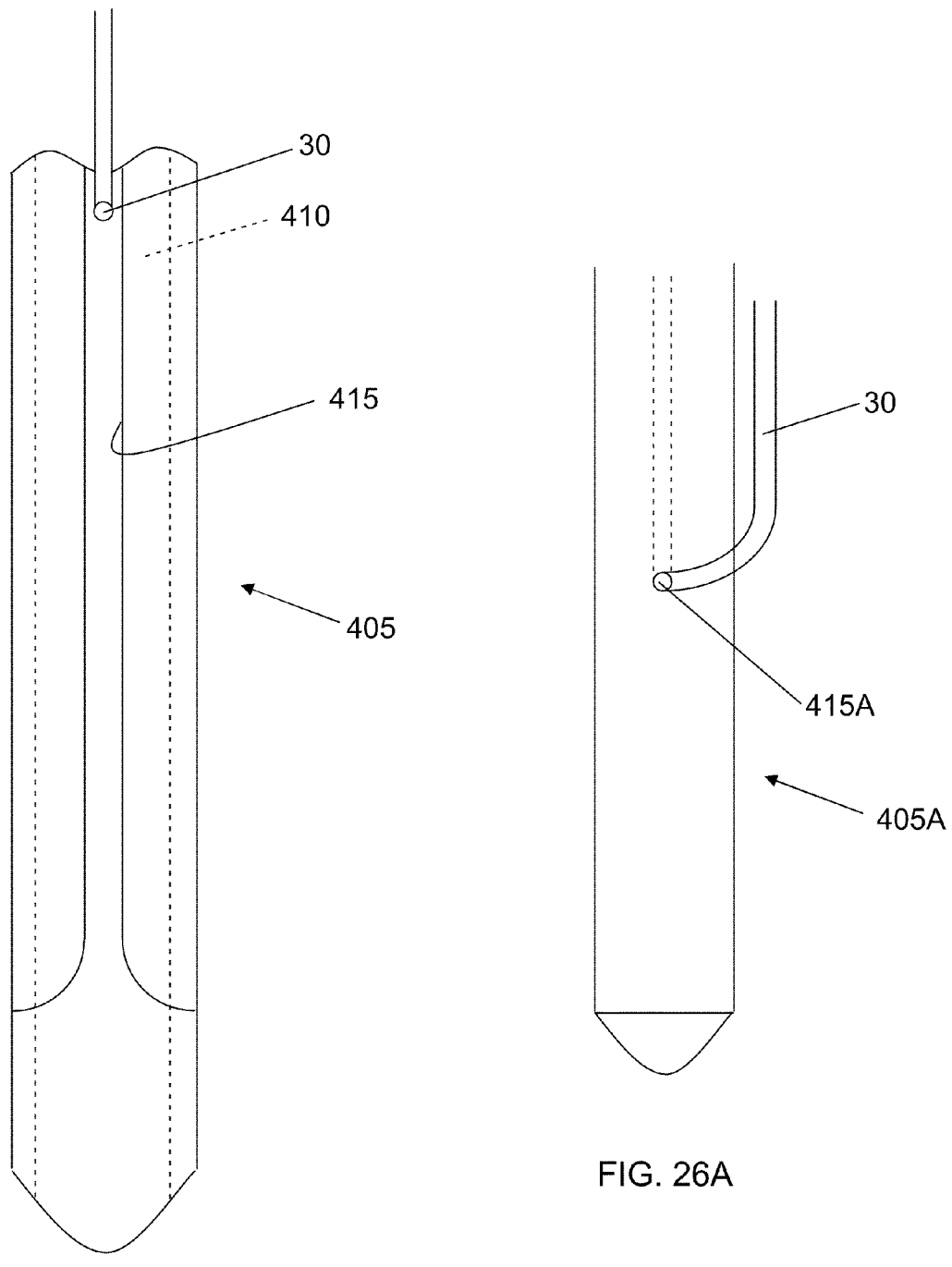
FIG. 26A is a schematic view of another suture threader formed in accordance with the present invention.

Looking next at FIGS. 25 and 26, there is shown a suture threader 405 which may be used to attach a suture 30 to anchor 335. Suture threader 405 comprises a hollow cannula having an interior lumen 410 and a slot 415 formed in its distal end. A suture 30 may be threaded down interior lumen 410, out slot 415 and then back alongside the exterior of the suture threader, in the manner shown in FIGS. 25 and 26. As a result of the natural resiliency of suture 30, a portion of distal loop 135 of suture 30 will stand laterally displaced from the hollow cannula, such that it can be caught by one of the flexible crossbars 390.

FIG. 26A shows a suture threader 405A generally similar to suture threader 405 shown in FIGS. 25 and 26, except that slot 415 is replaced by a hole 415A.

Figure 27:
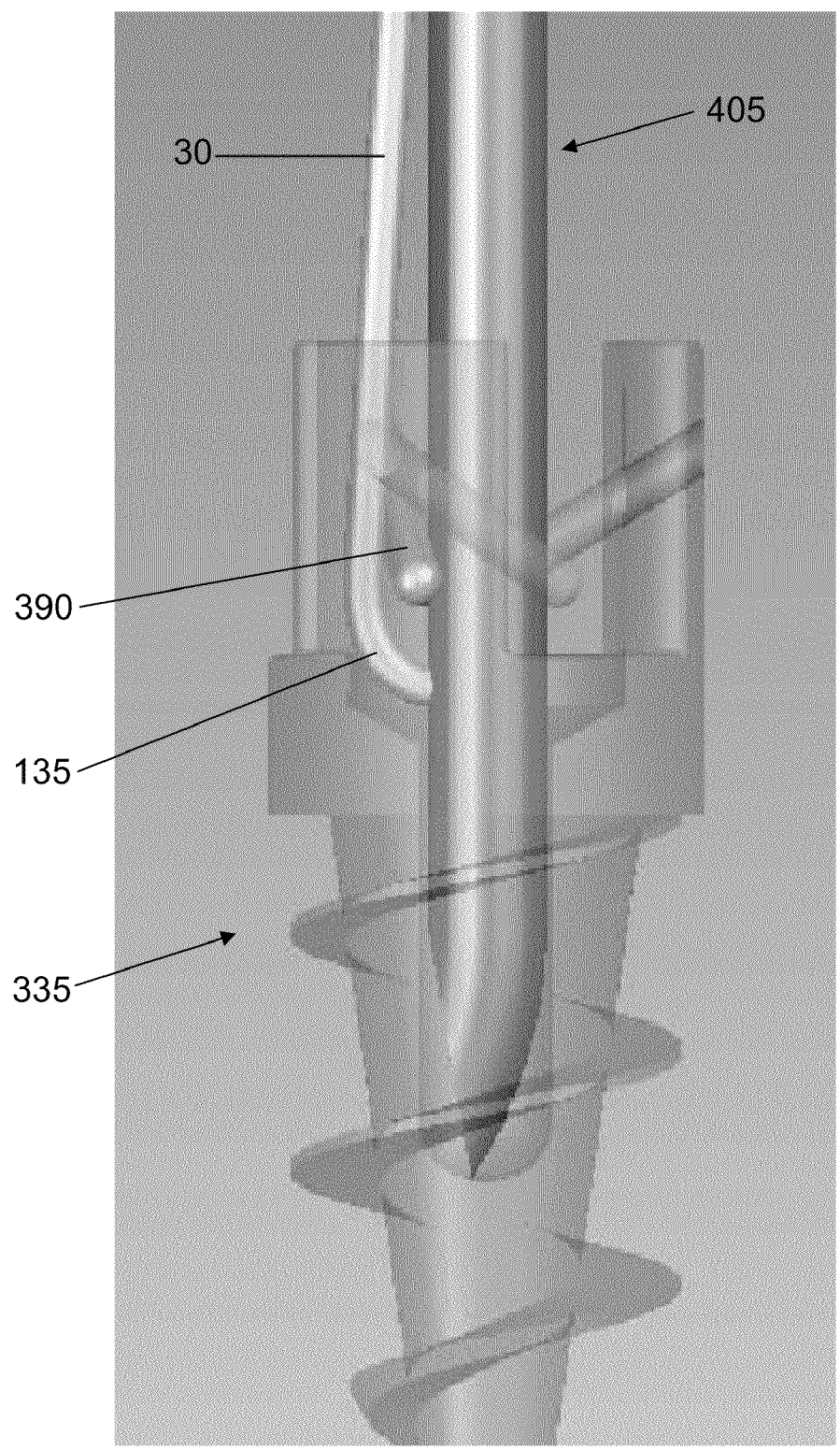
FIGS. 27-29 are schematic views showing a method of using the anchor of FIGS. 23 and 24 and the suture threader of FIGS. 25 and 26.
Figure 28:
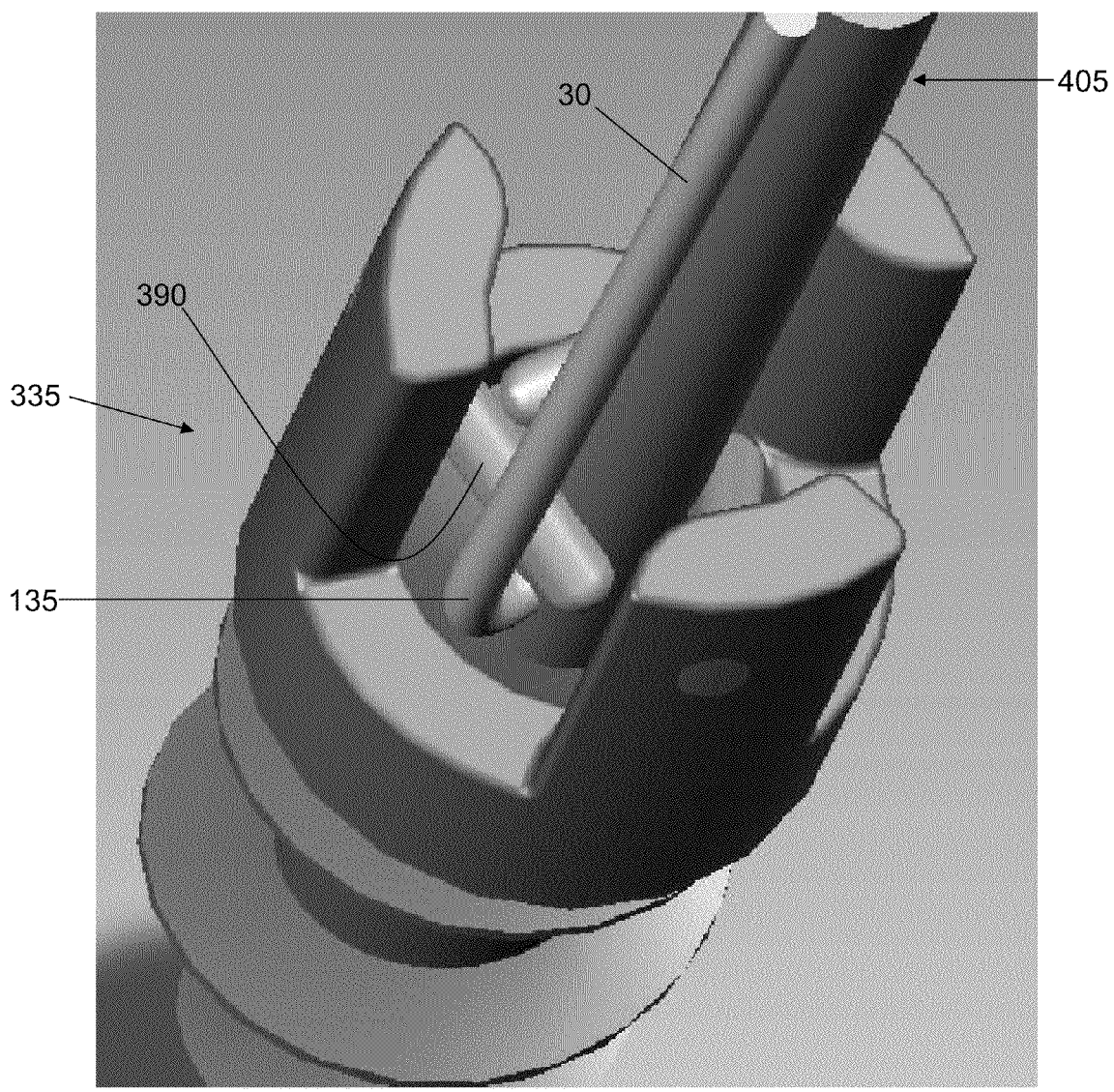
Figure 29:
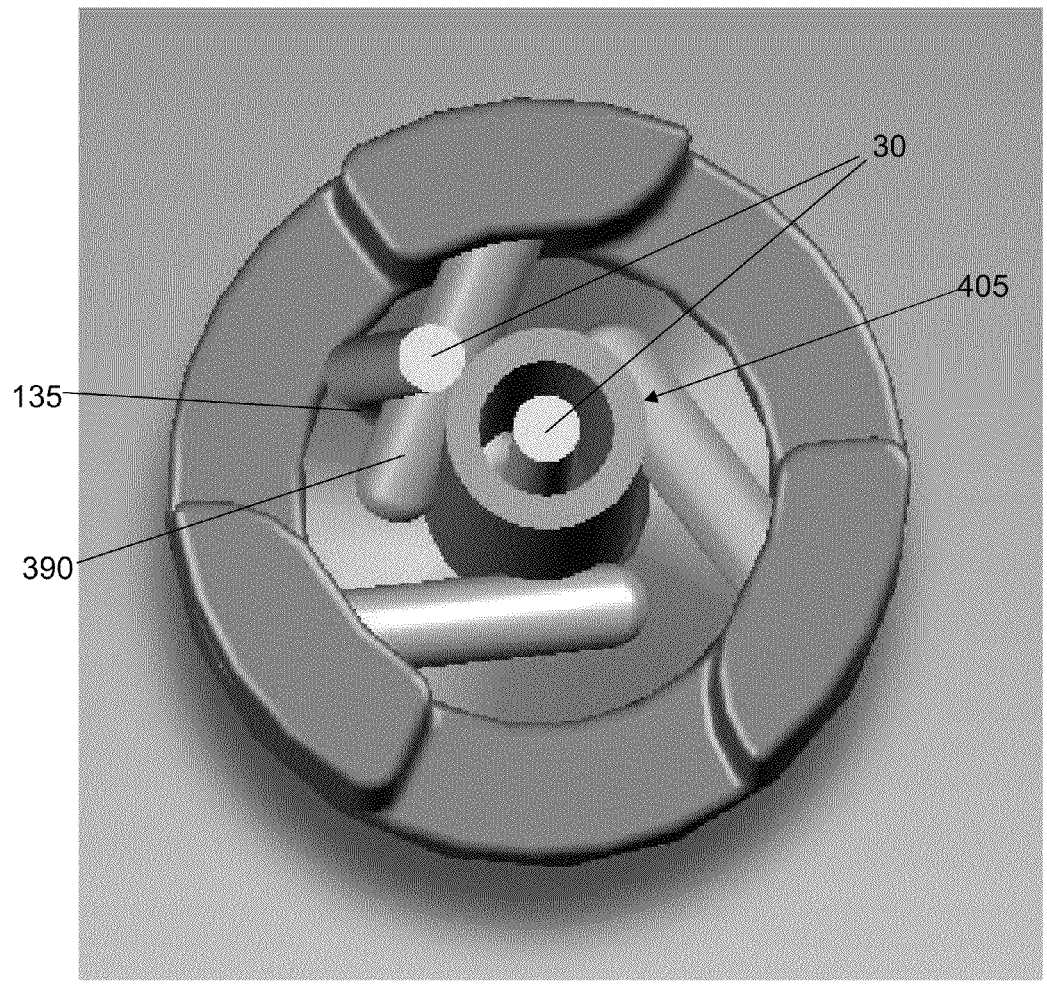

In use, and looking now at FIGS. 27-29, anchor 335 is screwed into the bone, and then a suture 30 is attached to anchor 335 using suture threader 405. This is done by advancing the distal end of suture threader 405 into axial recess 385 of anchor 335 until suture loop 135 slips over free end 400 of a flexible crossbar 390. Then suture threader 405 is retracted, leaving suture 30 attached to anchor 335.

Thus it will be seen that anchor 335 and suture threader 405 permit anchor 335 to be deployed in bone and a suture to be thereafter attached to that anchor, so that soft tissue may be attached to the bore using the anchor and suture.

As discussed above, the screw threads of the various anchors disclosed above serve to secure the anchor to the bone. However, it should also be appreciated that other mechanisms may be used to secure the body of the anchor to the bone. Thus, by way of example but not limitation, barbs, ribs, teeth and/or other anchor-securing mechanisms of the sort well known in the art may be incorporated on the body of the suture anchor so as to ensure that the suture anchor remains secured in the bone. In addition to the foregoing, other approaches can be used to secure the body of the anchor in the bone, e.g., the body can be hammered into the bone like a nail, or the anchor can be toggled upon entry into the bone so as to prevent its withdrawal, etc.

Figure 30:
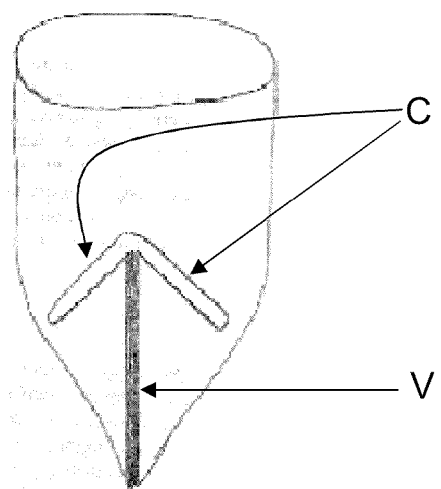
FIGS. 30-33 are schematic views illustrating suture receiving mechanisms for capturing a suture to an anchor in accordance with the present invention.
Figure 31:
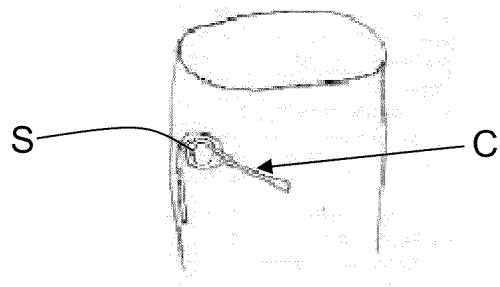
Figure 32:
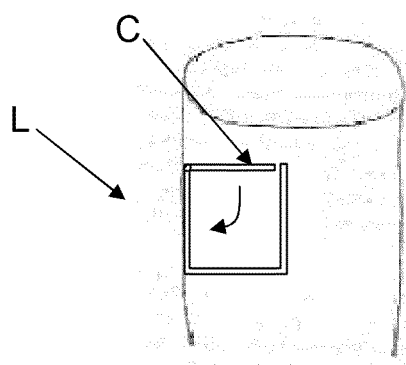

It should also be appreciated that, for the aforementioned constructions utilizing a flexible crossbar (e.g., anchors 200 and 335), alternative means may be provided for supporting the flexible crossbar on the anchor. Thus, by way of example but not limitation, and looking now at FIGS. 30-32, one or more flexible crossbars C may be supported on a vertical post V (FIG. 30), one or more vertical crossbars C may be formed as part of a spring clip S (FIG. 31) and one or more vertical crossbars C may be formed as part of a spring latch L (FIG. 32).

Figure 33:
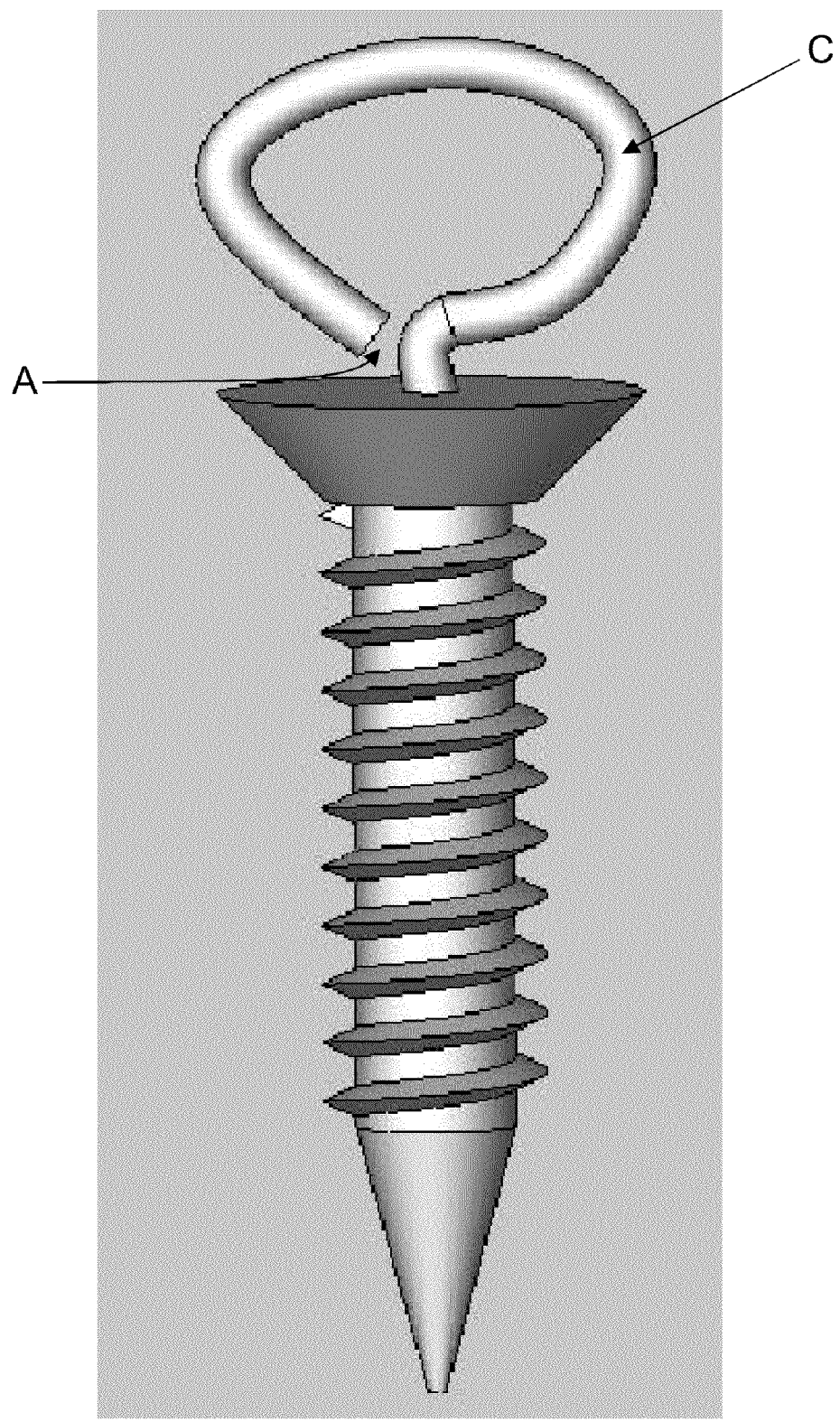

Furthermore, and looking now at FIG. 33, the crossbar need not be flexible, provided that the crossbar forms a tortuous pathway which restricts suture disengagement. Thus, for example, in FIG. 33, crossbar C is shown in the form of an eyelet having a restricted access point A.

Thus it will be seen that the suture may be attached to the anchor by a variety of means including a post, buckle, pulley, hook, spring, carabineer, latch or any other suture-receiving mechanism that is capable of securing suture to the anchor at one or more points within or on the anchor.

Looking next at FIGS. 34-36, there is shown a suture threader 500 which may be used in conjunction with any of the anchors discussed above. Suture threader 500 generally comprises a shaft 505 terminating in a distal tip 510. Shaft 505 is cut along its distal end so as to produce a pair of parallel fingers 515, 520 which are separated intermediate their length by a slot 525. A surface groove 530 is formed in finger 515 for receiving suture 30. Another surface groove 535 is formed in finger 520 for receiving another portion of suture 30. Suture seats 540 are formed at the distal ends of fingers 515, 520 so as to support suture 30 as it passes from surface groove 530 to surface groove 535. Thus, it will be appreciated that suture 30 will be configured in a U-shape in the region where suture 30 passes from surface groove 530 and into surface groove 535.

Suture threader 500 may be used to capture suture to an anchor in the manner discussed above, e.g., by moving suture 30 distally so as to engage a crossbar and then moving the suture threader proximally so as to snare suture 30 on the crossbar.

Looking next at FIGS. 38-43, there is provided a suture 600 comprising one or more suture loops 605 and one or more free ends 610. Suture loops 605 may be interlocking or independent of one another.

Figure 40:
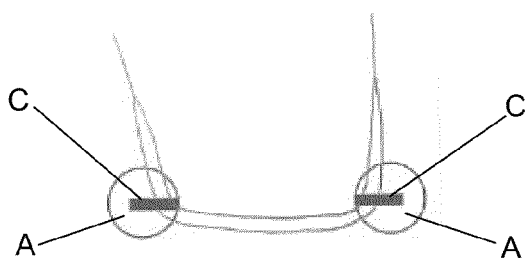
Figure 41:
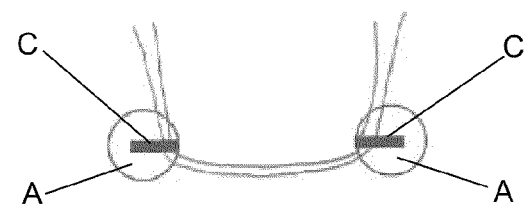
Figure 42:
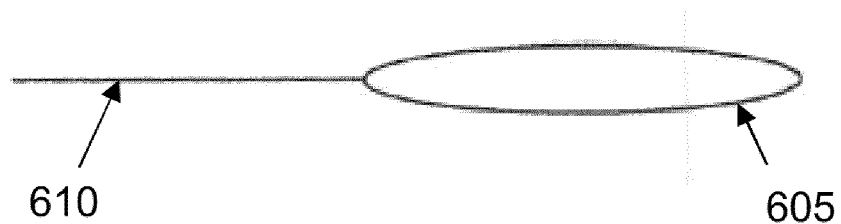
Figure 43:
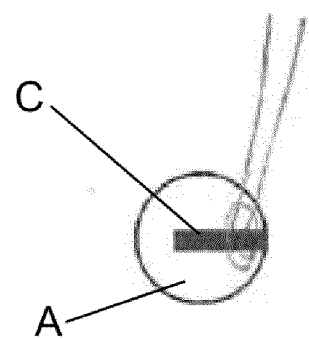

Each of the free ends 610 may be passed through soft tissue and around a respective crossbar via a suture threader. The suture can then be pulled through the anchor such that the suture loop is disposed on either side of the crossbar C of anchor A (FIG. 40). The ends of the suture loop can then be cut to create two additional free ends of suture emanating from the anchor that can be used independently in the soft tissue repair (FIG. 41).

Figure 44:
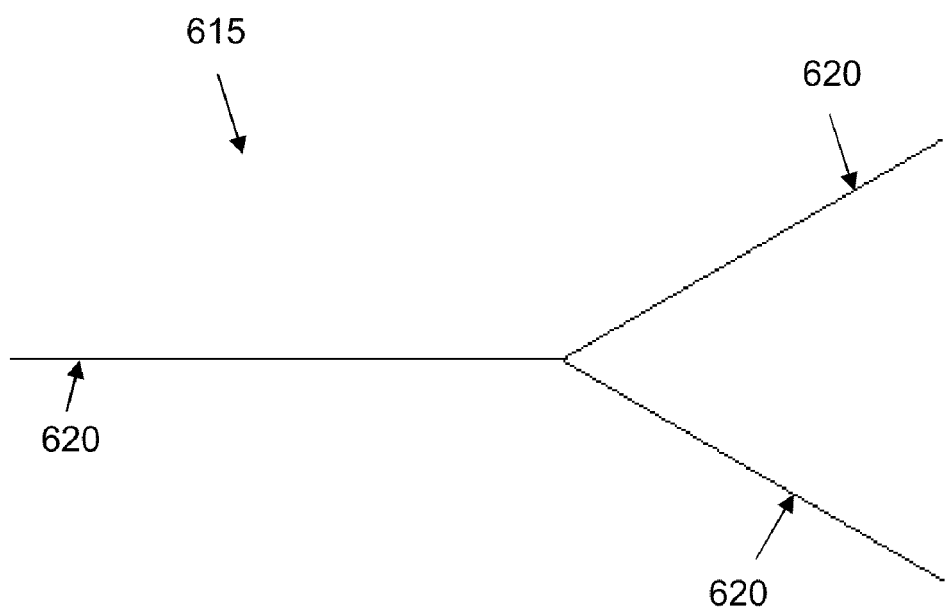
Figure 45:
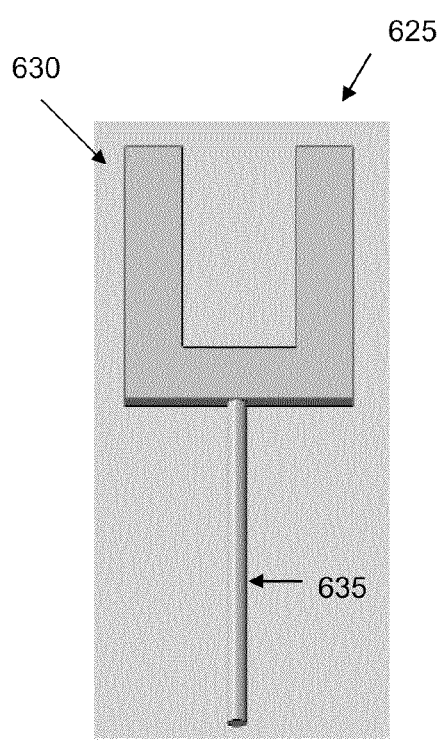
Figure 46:
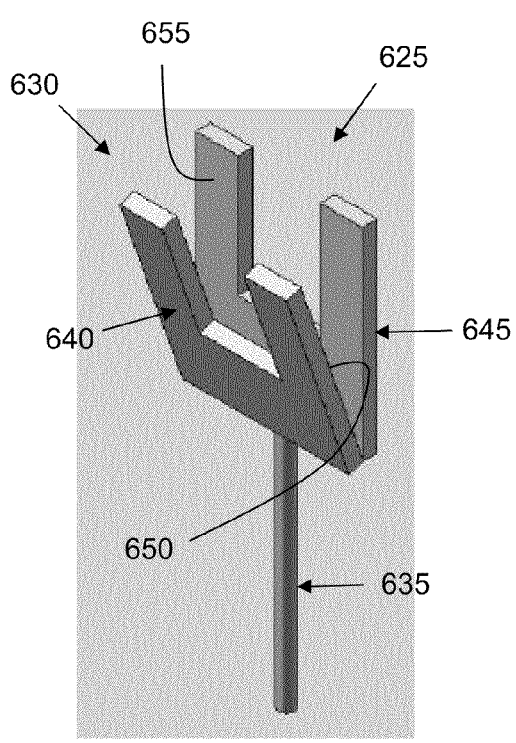

Looking next at FIG. 44, there is provided suture 615 comprising three free, unencumbered ends 620. Each of the free ends 620 of suture 615 can be pulled through an anchor such that multiple strands of suture are disposed on either side of a crossbar. Suture 620 can then be used to thread one or more additional anchors in the same manner. Suture 620 can then be cut at or near the intersection of the multiple suture strands such that two or more free ends of suture are emanating from the anchor that can be used independently in the soft tissue repair.

These suture designs are applicable in situations in which the surgeon would, absent these suture designs, otherwise have to pass suture through tissue multiple times to get more than one free end of suture emanating from an anchor. These suture designs allow the surgeon to make one pass through tissue and into an anchor and, by cutting the suture, have multiple free ends of suture to use independently in the soft tissue repair.

Looking next at FIGS. 45-48, there is shown a soft tissue grasping mechanism 625 comprising a tip 630 and a shaft 635 which connects tip 630 to a handle (not shown). Tip 630 comprises a top portion 640 and a bottom portion 645. The handle is configured to open and close top portion 640 and bottom portion 645 so as to grasp tissue and clamp it between inner surface 650 of top portion 640 and inner surface 655 of bottom portion 645. The handle is also configured to position top portion 640 and bottom portion 645 up or down so as to angle tip 630 relative to shaft 635.

One or both of inner surfaces 650 and inner surface 655 may comprise teeth-like elements to enhance the grip on soft tissue when clamping soft tissue between the top and bottom portions of tip 630. Tip 630 may also have fork-like tines extending therefrom for enhancing the grip on soft tissue.

Preferably, the handle is ergonomically designed so as to allow a surgeon to comfortably grip soft tissue grasping mechanism 625.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A suture anchor, comprising:
a body having a proximal end, a distal end, an outer surface, an axial recess extending from the proximal end toward the distal end, and a transverse edge;
a bone engaging element extending from the outer surface of the body for engagement with bone; and
a crossbar extending from the body and across the axial recess such that the crossbar has a free end and a fixed end and the free end of the crossbar is normally disposed distally of the transverse edge of the body,
wherein the crossbar is flexible such that when a distally directed force is applied to the crossbar, the free end of the crossbar is positionable in the axial recess and when a proximally directed force is applied to the crossbar, the free end of the crossbar is engageable with the transverse edge to limit proximal motion of the crossbar,
wherein the body has a crossbar window positioned between the proximal end and the distal end of the body in communication with the axial recess, wherein the crossbar window has a proximal side and a distal side, and wherein the proximal side of the crossbar window defines the transverse edge of the of the body.

2. The suture anchor of claim 1 wherein the free end of the crossbar is normally disposed in the crossbar window.

3. The suture anchor of claim 1, wherein the crossbar extends from the body at an angle such that the free end of the crossbar is normally disposed distally to the fixed end of the crossbar.

4. The suture anchor of claim 1, wherein the axial recess is configured to receive a driver for deploying the anchor in bone.

5. The suture anchor of claim 4, wherein the axial recess is non-circular so as to permit the anchor to be rotationally driven by a driver.

6. A suture anchor, comprising:
a body having a proximal end, a distal end, an outer surface, an axial recess extending from the proximal end toward the distal end, and a transverse edge;
a bone engaging element extending from the outer surface of the body for engagement with bone; and
a crossbar extending from the body and across the axial recess such that the crossbar has a free end and a fixed end and the free end of the crossbar is normally disposed distally of the transverse edge of the body,
wherein the crossbar is flexible such that when a distally directed force is applied to the crossbar, the free end of the crossbar is deflected relative to the fixed end and positioned in the axial recess and when a proximally directed force is applied to the crossbar, the free end of the crossbar engages the transverse edge to limit proximal motion of the crossbar.

7. The suture anchor of claim 6, wherein the body has a crossbar window positioned between the proximal end and the distal end of the body in communication with the axial recess, wherein the crossbar window has a proximal side and a distal side, and wherein the proximal side of the crossbar window defines the transverse edge of the of the body.

8. The suture anchor of claim 7, wherein the free end of the crossbar is normally disposed in the crossbar window.

9. The suture anchor of claim 6, wherein crossbar extends from the body at an angle such that the free end of the crossbar is normally disposed distally to the fixed end of the crossbar.

10. The suture anchor of claim 6, wherein the axial recess is configured to receive a driver for deploying the anchor in bone.

11. The suture anchor of claim 10, wherein the axial recess is non-circular so as to permit the anchor to be rotationally driven by a driver.

* * * * *